US009550072B2

(12) United States Patent
Trujillo et al.

(10) Patent No.: US 9,550,072 B2
(45) Date of Patent: Jan. 24, 2017

(54) DIAGNOSTIC DEVICE, THERAPEUTIC DEVICE, AND USES THEREOF

(71) Applicant: Cerca Solutions, LLC, Rockville, MD (US)

(72) Inventors: Jose Roberto Trujillo, Rockville, MD (US); Fernando de Moraes Mendonça Ribeiro, Sao Carlos (BR)

(73) Assignee: CERCA SOLUTIONS, LLC, Rockville, MD (US)

( * ) Notice: Subject to any disclaimer, the term of this patent is extended or adjusted under 35 U.S.C. 154(b) by 313 days.

(21) Appl. No.: 13/829,686

(22) Filed: Mar. 14, 2013

(65) Prior Publication Data
US 2014/0039322 A1 Feb. 6, 2014

Related U.S. Application Data

(60) Provisional application No. 61/679,444, filed on Aug. 3, 2012.

(51) Int. Cl.
| | | |
|---|---|---|
| A61B 8/00 | (2006.01) |
| A61N 5/06 | (2006.01) |
| A61B 5/00 | (2006.01) |
| A61B 1/303 | (2006.01) |
| A61B 1/00 | (2006.01) |
| A61B 1/04 | (2006.01) |
| A61B 1/06 | (2006.01) |

(52) U.S. Cl.
CPC ........... *A61N 5/062* (2013.01); *A61B 1/00186* (2013.01); *A61B 1/043* (2013.01); *A61B 1/06* (2013.01); *A61B 1/0638* (2013.01); *A61B 1/303* (2013.01); *A61B 5/0071* (2013.01); *A61B 5/4331* (2013.01)

(58) Field of Classification Search
CPC .............................. A61B 5/0071; A61B 5/062
See application file for complete search history.

(56) References Cited

U.S. PATENT DOCUMENTS

| | | | |
|---|---|---|---|
| 4,905,670 A * | 3/1990 | Adair ............................ 600/104 |
| 4,992,257 A | 2/1991 | Bonnett et al. |
| 5,162,519 A | 11/1992 | Bonnett et al. |
| 5,399,583 A | 3/1995 | Levy et al. |
| 5,421,339 A * | 6/1995 | Ramanujam ......... A61B 5/0071 600/477 |
| 5,458,595 A | 10/1995 | Tadir et al. |
| 5,522,868 A * | 6/1996 | Buckley et al. ................ 607/94 |
| 5,773,609 A | 6/1998 | Robinson et al. |
| 6,081,740 A * | 6/2000 | Gombrich et al. ........... 600/424 |

(Continued)

FOREIGN PATENT DOCUMENTS

WO WO 2009/072856 A1 6/2009

OTHER PUBLICATIONS

Agostinis et al., "Photodynamic Therapy of Cancer: An Update," *CA Cancer J. Clin.*, vol. 61, pp. 250-281 (2011) (Abstract only) (4 pages).

(Continued)

*Primary Examiner* — Long V Le
*Assistant Examiner* — Bradley Impink
(74) *Attorney, Agent, or Firm* — Bookoff McAndrews, PLLC

(57) ABSTRACT

Apparatus, method, computing devices, and computer programs related to photodiagnosis and photodynamic therapy, methods of use thereof, and a method for detecting abnormal tissue, are provided.

20 Claims, 24 Drawing Sheets

(56) References Cited

U.S. PATENT DOCUMENTS

| | | | |
|---|---|---|---|
| 6,645,230 | B2 | 11/2003 | Whitehurst |
| 7,351,242 | B1 | 4/2008 | Neuberger et al. |
| 7,355,155 | B2* | 4/2008 | Wang .......................... 250/205 |
| 2002/0065468 | A1* | 5/2002 | Utzinger ............ A61B 1/00186 600/476 |
| 2003/0218880 | A1* | 11/2003 | Brukilacchio ......... A61N 5/062 362/293 |
| 2004/0147843 | A1 | 7/2004 | Bambot et al. |
| 2005/0234526 | A1* | 10/2005 | Gilhuly et al. ................. 607/86 |
| 2008/0065003 | A1* | 3/2008 | Neuberger ........... A61N 5/0601 604/21 |
| 2011/0295186 | A1* | 12/2011 | Klem ............................. 604/20 |
| 2012/0232408 | A1 | 9/2012 | Weller-Brophy |

OTHER PUBLICATIONS

Allison at al., "Photosensitizers in Clinical PDT," *Photodiagn. Photodyn. Ther.*, vol. 1, pp. 27-42 (2004) (16 pages).

Herfs et al., "A Discrete Population of Squamocolumnar Junction Cells Implicated in the Pathogenesis of Cervical Cancer," *Proc. Natl. Acad. Sci.*, vol. 109, pp. 10516-10521 (2012) (7 pages).

International Search Report for PCT/US2013/053459 (published as WO 2014/022792), dated Oct. 12, 2013 (4 pages).

Walboomers et al., *J. Pathol.*, vol. 189, pp. 12-19 (1999) (8 pages).

\* cited by examiner

DIAGNOSTIC DEVICE, THERAPEUTIC DEVICE, AND USES THEREOF

CROSS-REFERENCE TO RELATED APPLICATION

This application claims benefit under 35 U.S.C. 119(e) to U.S. Provisional Patent Application 61/679,444, filed Aug. 3, 2012, which is incorporated by reference herein in its entirety.

BACKGROUND OF THE INVENTION

Field of the Invention

The present invention is related to photodiagnosis and photodynamic treatment.

Background Art

"Genital human papillomavirus (HPV) is the most common sexually transmitted infection (HPVI) in the United States. More than 40 HPV types can infect the genital areas of men and women, including the skin of the penis, vulva (area outside the vagina), and anus, and the linings of the vagina, cervix, and rectum. These types can also infect the lining of the mouth and throat. HPV types are often referred to as 'low-risk' (wart-causing) or 'high-risk' (cancer-causing), based on whether they put a person at risk for cancer. The International Agency for Research on Cancer found that 13 HPV types can cause cancer of the cervix; one of these types can cause cancers of the vulva, vagina, penis, anus, and certain head and neck cancers. The types of HPV that can cause genital warts are not the same as the types that can cause cancer." Centers for Disease Control, http://www.cdc.gov/cancer/hpv/basic_info/.

Certain HPV types are highly associated with cervical dysplasia and cervical cancer and are considered to be causative. Walboomers et al., *J. Pathology* 189:12-19 (1999). Annually, hundreds of thousands of women around the world die of cervical cancer, a condition that affects millions of women, especially those who are economically disadvantaged. Diagnosing and treating HPVI of the cervix and cervical dysplasia in their early stages will lower the incidence of cervical cancer, thus lowering its associated morbidity and mortality.

The current standard for diagnosis is the pathological examination of cervical tissue samples, e.g., the Papanicolaou test or "Pap smear" and biopsy with aid of colposcopy. However, these diagnostic methods require a delay between the time a tissue sample is taken and the time the test results are known. They also require at least one return visit for treatment. Moreover, in disadvantaged populations, these diagnostic methods simply are not available. When and where they are available, biopsies can present patient complications including local inflammation, pain, infection, and/or bleeding. In addition, the accuracy of the pathological examination is dependent on the pathologist's and doctor's training and experience. In addition, HPVI and cervical dysplasia can affect multiple sites of the exocervix and endocervix. Thus, a common problem in the diagnosis and treatment of cervical dysplasia and cancer is the failure to detect and treat all existing lesions.

There are several modalities for the treatment of cervical dysplasia and cancer, most of them involving variable degrees of surgical interventions such as $CO_2$ laser vaporization, cryotherapy, electrocautery, or local excision. Surgical removal of visible lesions is the most commonly modality and may result in patient complications. In addition, an inability to identify all existing lesions allows undetected HPVI and/or dysplasia to evolve into terminal cervical cancer. If the cervical dysplasia progresses to cervical cancer, more extensive surgical procedures are used, typically a hysterectomy and removal of lymph nodes. The entire diseased organ must be removed to assure that all microscopic disease is treated. Since the percentage of these lesions that will advance to a frankly malignant state is unknown and may be a minority of instances, indiscriminate destruction or surgical removal of the entire organ is, in fact, a radical and excessive treatment. For cervical cancer survivors, persistent local lesions, anatomical deformities secondary to surgical interventions, emotional and mental scarring, and other treatment sequalae increase public health costs. This burden is especially hard on emerging economies.

A device is needed for an accurate, noninvasive, rapid, and low cost method for diagnosing and for treating HPVI, cervical dysplasia, cervical precancer, and cervical cancer.

BRIEF SUMMARY OF THE INVENTION

Provided herein are devices that generally include a photodiagnostic component, and/or a photodynamic treatment component, and/or a control component. Such devices achieve numerous goals. For example, these devices allow for identification and/or treatment of abnormal tissue of the cervix.

In view thereof, disclosed herein is a photodiagnostic device which is generally designed to include a laser light source, a heat dissipation system, a lens to collimate light from the light source, an optic having a light pathway, a light filter attached to the light pathway to direct light from the lens to an end of the light pathway toward the cervical tissue, and a light filter attached to the light pathway adapted to separate a spectral region of light from a fluorescence of light reflected by the cervical tissue.

In another embodiment, disclosed herein is a photodynamic treatment device which is generally designed to include a light source, a heat dissipation system, a light guide attached to the device cover and adapted for vaginal insertion to direct light to cervical tissue, and a light protector that is attached to a distal end of the light guide adapted to surround the cervical tissue.

In another embodiment, disclosed herein is a photodiagnostic and photodynamic therapeutic device which is generally designed to include a photodiagnostic component including a laser light source, a lens, and a light filter, a photodynamic treatment component including a second light source and a light guide, and a control component attached to and providing power to the photodiagnostic component and the photodynamic treatment component, and controlling activation of the laser light source and the second light source.

In another exemplary embodiment, disclosed herein is a method of detecting autofluorescence of abnormal cervical tissue which generally includes generating excitation light from a laser light source, directing the excitation light towards cervical tissue, receiving reflected excitation light and fluorescent light from the cervical tissue and passing the reflected light and the florescent light through a light filter to separate the reflected light from the fluorescent light, and viewing the florescent light of abnormal cervical tissue.

In another exemplary embodiment, disclosed herein is a method of treating cervical tissue having a photosensitizer compound disposed thereon which generally includes selecting an appropriate dose of light energy, generating a light emission from the light source, and directing the light emission through a light guide to the cervical tissue for a selected period of time to deliver the selected dose of light energy.

In another exemplary embodiment, disclosed herein is a method of diagnosing and treating abnormal cervical tissue which generally includes: analyzing cervical tissue by generating a laser light emission, directing the light emission towards cervical tissue, passing the light emission through a light filter, and viewing the fluorescence of the cervical tissue to detect the presence of abnormal cervical tissue; and treating the abnormal cervical tissue having a photosensitizer compound disposed thereon by generating a second light emission and directing the second light emission through the cervical tissue to deliver a selected dose of light energy to destroy the abnormal cervical tissue.

BRIEF DESCRIPTION OF THE DRAWINGS/FIGURES

PARTS LIST

Figure 1:
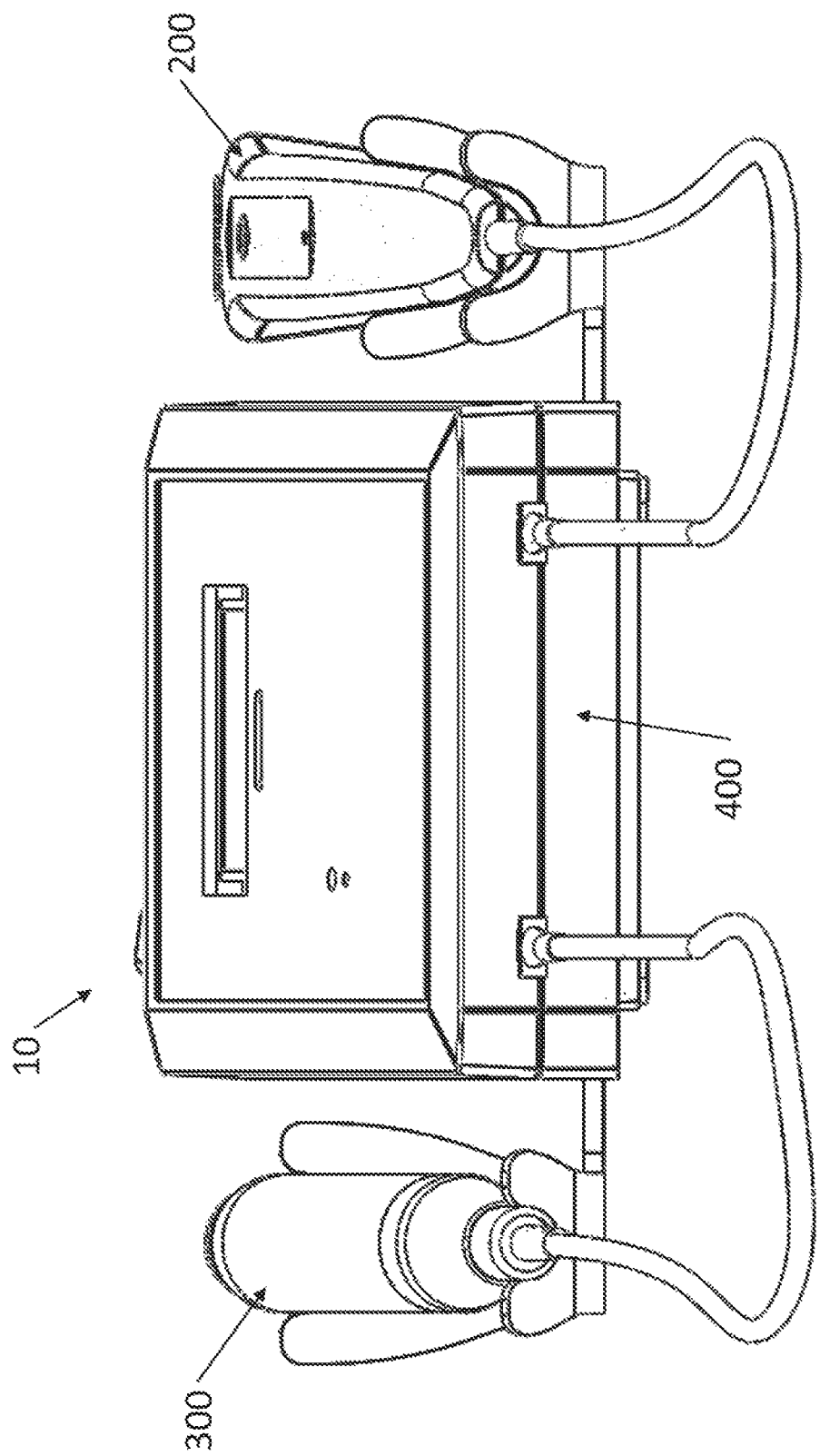
FIG. 1 is a perspective view of a photodiagnostic and photodynamic therapeutic device, in accordance with an exemplary aspect of the invention.

10—photodiagnostic and photodynamic therapeutic device
200—diagnostic component
202—power button
204—optic 204a—optic end
204b—optic end
210—optical support
212—anti-reflective filter
214—dichroic filter
216—notch filter
218—high pass filter
220—ring
222—finishing ring
230—collimator lens
232—laser diode
234—focus adjustment ring
236—heat dissipation system
240—circuit board
242—circuit board
250—diagnostic component shell
252—diagnostic component power cord
260—photographic camera
262—adapter ring
300—treatment component
304—light component
306—treatment component power cord
310—guiding sleeve nozzle
320—core metal plate
322—high-intensity LEDs
324—spacing ring
326—insulator ring
330—protective screen
334—heat sink ring
336—heat sink
350—treatment component shell
352—end cap
370—guiding sleeve
372—light protector
372a—light protector
372b—light protector
374—glass screen
376—rubber rings
378—protective sleeve
380—light guide
400—control component
402—power outlet
404—on-off switch
406—security key mechanism
408—control panel
410—display screen
412—operation button
414—operation button
416a—operation button
416b—operation button
420—diagnostic component support
430—treatment component support
450—control component shell
500—adjustable support
510—coupling
520—foldable leg
530—flexible rod
540—telescopic tube
540a—adjustment lock
542—telescopic tube
542a—adjustment lock
544—telescopic tube
600—computer system
602—display interface
604—processor
606—communication infrastructure
608—main memory
610—secondary memory
612—hard disk drive
614—removable storage drive
618—removable storage unit
620—interface
677—removable storage unit
624—network interface
626—communications path
628—signals
1010—photodiagnostic and photodynamic therapeutic device
1200—diagnostic component
1252—diagnostic component power cord
1300—treatment component
1304—light component
1306—treatment component power cord
1310—guiding sleeve nozzle
1320—core metal plate
1322—high-intensity LEDs
1324—spacing ring
1326—insulator ring
1330—protective screen
1334—heat sink ring
1336—heat sink
1350—treatment component shell
1352—end cap
1400—control component
1402—power outlet
1404—on-off switch
1408—control panel
1410—display screen
1412—operation button
1414—operation button
1416a—operation button
1416b—operation button
1418—cable support
1420—diagnostic component support
1422—interlock
1430—treatment component support
1450—control component shell
1460a—two way connector
1460b—four way connector
1500—adjustable support
1502a—cable support
1502b—cable support
1504a—control component support
1504b—control component support
1510—coupling
1520a—adjustment lock
1530—flexible rod
1542—telescopic member
1542a—adjustment lock
1600—mobile base
1602—wheels
1620—feet

DETAILED DESCRIPTION OF THE INVENTION

The present invention is related to the detection, diagnosis, and treatment of abnormal tissue of the cervix. In one aspect, this invention uses noninvasive photodynamic methods to differentiate healthy tissue from abnormal tissue using photodiagnosis. In one aspect, this invention uses a similar photodynamic method to provide photodynamic treatment (PDT) for the abnormal tissue. In some aspects, the invention is a device that includes a diagnostic component. The diagnostic component is specially adapted for detection of abnormal tissue of the cervix. In some aspects, the invention is a device that includes a treatment component. The treatment component is specially adapted for treatment of abnormal tissue of the cervix. In some aspects, the invention is a device that includes both a diagnostic component and a treatment component. In some aspects, a device of the invention includes a control component including a control panel to operate the diagnostic component and/or the treatment component. In some aspects, the invention is diagnostic and/or treatment methods using a device described herein. In some aspects, the invention is a method for providing photodiagnosis of cervical tissue by detecting tissue autofluorescence, tissue fluorescence after application of a photosensitizer compound, and/or tissue fluorescence after photodynamic treatment. In some aspects, the invention is a method for providing photodiagnosis of cervical tissue before and after photodynamic treatment of the cervical tissue. In some aspects, the invention is a method of treating abnormal tissue of the cervix.

Based upon preliminary clinical evaluations, the present diagnostic component allows, for the first time, the identification and diagnosis of abnormal tissue without the use of a photosensitizer (PS). In addition, the treatment component has been used successfully to treat twenty-three patients having cervical precancer or cancer. Further, based upon preliminary evaluations, the treatment component is expected to be able to treat abnormal tissue such as precancer and cancer up to 1 cm deep, and possibly deeper, in and near the cervix. See also Example 4.

As discussed herein, "abnormal tissue" shall refer to tissue having abnormal cell growth or other detectable abnormalities resulting from, e.g., infections with microorganisms such as HPV, or from a precancerous, a cancerous state, or other hyperproliferative states. Abnormal tissue includes cervical intraepithelial neoplasia (CIN), cervical intraepithelial lesion(s) (SIL), cervical cancer (cervical squamous cell carcinoma and cervical adenocarcinoma) and other hyperproliferative tissue.

The present invention concerns a diagnostic component for illuminating the cervix with a light source to detect differences between healthy tissue and abnormal tissue. The diagnostic component detects fluorescence indicating abnormal tissue having, e.g., abnormal cell growth. The structure and biochemical composition of tissue affects its interaction with light, such that healthy tissue presents optic characteristics distinctive from those seen in abnormal tissue. Conditions such as infection, cervical dysplasia, and cancer change the composition of the affected cells, which in turn, changes their interaction with light. Optical methods for the diagnosis of tissue abnormalities have a substantial advantage of being noninvasive and having minimal, if any, side effects. In addition, the present invention allows for immediate diagnosis, in contrast to diagnosis using currently available methods such as the Pap smear.

The diagnostic component is specially adapted for the cervix and includes a light source, such as a low intensity laser diode. In some aspects of the invention, the light source generates light at a defined wavelength and a defined intensity. As discussed herein, the low intensity laser diode is capable of outputting a light intensity ranging from approximately 0 mW/cm$^2$ to approximately 100 mW/cm$^2$. Furthermore, the low intensity laser diode is capable of outputting a light intensity ranging from approximately 15 mW/cm$^2$ to approximately 24 mW/cm$^2$. In some aspects of the invention, the diagnostic component includes a heat dissipation system to regulate the temperature of the light source.

In some aspects, the diagnostic component can include an optic having a light pathway, and one or more lenses and/or one or more filters and/or one or more mirrors attached to the light pathway. In some aspects, the diagnostic component can include a collimator lens to collect and collimate the generated light. In some aspects, the diagnostic component can include a filter or dichroic mirror to direct the light toward cervical tissue. In some aspects, the diagnostic component can include a second filter to separate a spectral region of the light from the fluorescence of the light reflected by the cervical tissue to better analyze light returning from the cervical tissue. The diagnostic component can generate a light beam approximately 20 mm in diameter.

In some aspects, the present invention is a component for treating abnormal tissue of and near the cervix. The treatment component illuminates an area for treatment of the abnormal tissue using photodynamic therapy. In photodynamic therapy, photosensitizers (PS) are used in combination with light irradiation at specific wavelengths to induce oxidative damage in abnormal, e.g., hyperproliferative tissues. It is thought that abnormal, e.g., hyperproliferative, tissues selectively retain PS and that subsequently induced oxidative damage is localized to areas of PS accumulation.

Numerous types of PS have been evaluated and shown to be at least partially effective for photodynamic therapy. Known photodynamic therapy PS include psoralens, porphyrins, chlorins, bacteriochlorins, pheophorbide, bacteriopheophorbide and phthalocyanins, as well as precursors to protoporphyrin IX (PpIX) such as 5-aminolevulinic acid (ALA), methyl aminolevulinic acid (MAL), and hexyl aminolevulinic acid (HAL), which are converted intracellularly to PpIX. PS compounds are generally administered in a carrier such as a cream or gel. PS compounds and their carriers are further described below.

The treatment component is specially adapted for the cervix and includes a light source, such as a high intensity light emitting diode (LED) light source, and a light guide to transmit the light to the defined area. In one aspect of the invention, the defined area is approximately 20 mm in diameter. In addition, the treatment component can include a protective sleeve surrounding the light guide to allow for vaginal insertion, and a ring between the light guide and a protective sleeve to center the protective sleeve on the light guide and to provide a biological barrier between the cervical tissue and the light source As used herein, the high intensity LED is a LED array that is capable of outputting a light intensity ranging from approximately 0 mW/cm$^2$ to approximately 250 mW/cm$^2$. Furthermore, the high intensity LED is capable of outputting a light intensity ranging from approximately 40 mW/cm$^2$ to approximately 120 mW/cm$^2$. In one aspect of the invention, this light intensity range is established to adapt the energy to specific doctor protocols. In one aspect of the invention, the treatment component includes a heat dissipation system attached to the light source to regulate the temperature of the light source.

Prior to treatment, a PS compound is applied to the abnormal tissue so that, upon illumination from the treatment component, the abnormal cells and tissue are destroyed. As is well known in the art, different PS compounds require light of different wavelength for photodynamic therapy. After application to the patient's affected area, the photosensitizer is allowed to penetrate the affected area for a period of approximately 8 to approximately 30 minutes. As is well known in the art, different PS and carriers will require differing lengths of time to penetrate, and the optimal penetration time can easily be determined.

For example, the PS compound can also be allowed to penetrate the affected area for a period of approximately 60 to approximately 180 minutes. In an alternate aspect of the invention, the PS compound can be allowed to penetrate the affected area for a period of approximately 8 to approximately 180 minutes.

In some aspects of the invention, the treatment component includes a light source to generate light at a defined wavelength and a defined intensity to treat abnormal cervical tissue containing a PS. In some aspects of the invention, the treatment component can include a light guide to direct the light toward the abnormal cervical tissue and a light protector to surround the cervical tissue and protect nearby anatomical structures from the generated light. In some aspects of the invention, the light protector can also conform to the anatomical variations of the cervix in different patients.

In some aspects of the invention, after treatment, the diagnostic component can be used to verify the efficacy of treatment. In some aspects of the invention, the PS compound can also be reapplied to verify that all abnormal tissues have been destroyed. In some aspects of the invention, residual abnormal tissue can be retreated with additional photodynamic treatments for, e.g., a total of 2, 3, 4, 5, 6, 7, 8, 9, or 10 treatments.

In some aspects of the invention, the diagnostic component and/or treatment component can be hand held. In some aspects, the diagnostic component is self-contained. In some aspects, the diagnostic component is part of a larger device. In some aspects, the treatment component is self-contained. In some aspects, the treatment component is part of a larger device. In some aspects, a device including either a diagnostic component or a treatment component also includes a control component. In some aspects of the invention, a device includes both a diagnostic component and a treatment component. In some aspects, a device that includes both a diagnostic component and a treatment component also includes a control component. In some aspects, a device including a diagnostic component and/or a treatment component can be portable.

In some aspects, the present invention is a device that includes a diagnostic component and/or a treatment component. In some aspects, the device also includes a control component. In some aspects, the control component provides power to the diagnostic component and/or the treatment component. In some aspects, the control component includes a control panel that operates the diagnostic component and/or the treatment component. In some aspects, the control panel can include a display screen and input buttons that control activation of the diagnostic component and/or the treatment component. In some aspects, the control panel can also allow for selection of a particular light intensity and duration of light intensity for the diagnostic component and/or the treatment component. In some aspects of the invention, the control panel can allow for selection of a particular light wavelength for the diagnostic component and/or the treatment component.

It is well known in the art that each photosensitizer is activated by a specific wavelength of light. See, e.g., U.S. Pat. No. 6,645,230 B2. Therefore, use of different photosensitizers can require use of different LEDs in the treatment component to produce the desired wavelength. The photosensitizer is mixed into a suitable carrier, such as cream or gel, for application to the abnormal tissue in the cervical area. The carrier can include DMSO and EDTA to enhance efficacy. Several PS creams and gels are commercially available. An example that contains MAL is METVIX (Galderma). The percent or dose of sensitizer compound is readily determined based upon knowledge in the art. For example, ALA and MAL are commonly used at a 20% concentration. Photosensitizers may be used alone or in combination, for example, a mixture of ALA and MAL in a range of ratios from approximately 0% ALA and approximately 100% MAL to approximately 100% ALA and 0% MAL.

Metatetra(hydroxyphenyl)chlorin ("m-THPC") is a photosensitizer shown to be effective in PDT of cancer, especially for advanced head and neck squamous cell carcinoma. Some other commonly used porphyrins for photodynamic therapy are hematoporphyrin IX (HpIX) and hematoporphyrin derivative (HpD). U.S. Pat. No. 4,992,257 and U.S. Pat. No. 5,162,519 disclose the use of select dihydroporphyrins and tetrahydroporphyrins, including m-THPC, to induce necrosis (tissue death) in tumors. U.S. Pat. No. 5,399,583 discloses a limited group of hydromonobenzo porphyrins, or "green porphyrins," which are photoactive at relatively long wavelengths thought to penetrate deeper into body tissues which may allow for the use of lower doses of green porphyrins in PDT. Additional photosensitizers are also known. E.g., U.S. Pat. No. 5,458,595; U.S. Pat. No. 5,773,609; U.S. Pat. No. 6,645,230; U.S. Pat. No. 7,351,242; and Allison, et al., "Photosensitizers in clinical PDT," *Photodiagn. Photodyn. Ther.* 1:27-42 (2004).

Current clinically applied photosensitizers are provided in Table 2 of Agostinis, et al., "Photodynamic Therapy of Cancer: An Update," *CA Cancer J Clin,* 61: 250-281 (2011). Photosensitizer and corresponding wavelength information from Table 2 is provided below.

| Photosensitizer | Wavelength, nm |
| --- | --- |
| Porfimer sodium (Photofrin) (HPD) | 630 |
| ALA | 635 |
| ALA esters | 635 |
| Temoporfin (Foscan) (mTHPC) | 652 |
| Verteporfin | 690 |
| HPPH | 665 |
| SnEt2 (Purlytin) | 660 |
| Talaporfin (LS11, MACE, NPe6) | 660 |
| Ce6-PVP (Fotolon), Ce6 derivatives (Radachlorin, Photodithazine) | 660 |
| Silicon phthalocyanine (Pc4) | 675 |
| Padoporfin (TOOKAD) | 762 |
| Motexafin lutetium (Lutex) | 732 |

As mentioned above, one of ordinary skill in the art knows to match the wavelength of light to each different PS compound. For example, the optimal wavelength range for PpIX, ALA, MAL, and HAL is 615 nm to 635 nm and the optimal range for the hydromonobenzoporphyrins disclosed in U.S. Pat. No. 5,399,583 is 670 nm to 780 nm. Dihydroporphyrins and tetrahydro porphyrins disclosed in U.S. Pat. No. 4,992,257 and U.S. Pat. No. 5,162,519 require a wavelength of 652 nm to 653 nm.

In some aspects of the invention, a patient is treated for potential cervical dysplasia and/or cervical cancer by first analyzing the cervical tissue with a photodiagnostic device. If abnormal tissue is detected, a PS is applied to the cervical tissue. The PS is allowed to penetrate the cervical tissue for 60-180 minutes before applying photodynamic treatment. Optionally, a photodiagnostic device can be used to verify that the PS is selectively utilized by the abnormal tissue and to confirm readiness of the cervical tissue for treatment. A selected dose of light energy is then administered to the cervical tissue to destroy the abnormal tissue. The selected dose of light energy can be specified from a range of light intensities and treatment times, from approximately 0 mW/cm² to approximately 250 mW/cm², and approximately 0 minutes to approximately 90 minutes. Alternatively, a fixed dose of light energy can be selected from a number of pre-programmed options that provide varying light intensity and treatment time combinations. After photodynamic treatment, the photodiagnostic device can be used again to verify the efficacy of the photodynamic treatment in destroying the abnormal tissue.

The following detailed description of a photodiagnostic and photodynamic therapeutic device refers to the accompanying figures that illustrate exemplary embodiments. Other embodiments are possible. Modifications can be made to the embodiments described herein without departing from the spirit and scope of the present invention. Therefore, the following detailed description is not meant be limiting.

Figure 2:
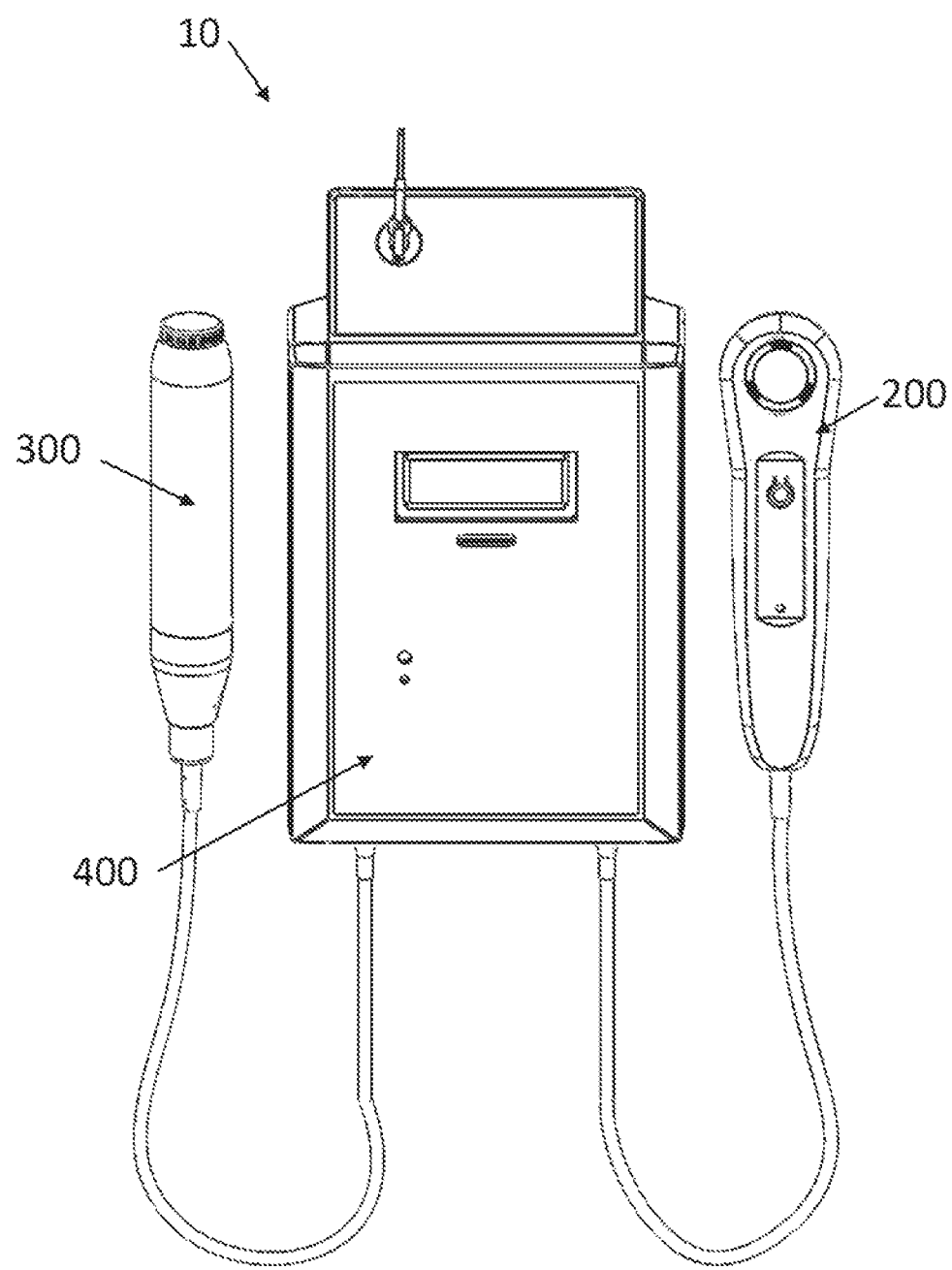
FIG. 2 is a top view of a photodiagnostic and photodynamic therapeutic device, in accordance with an exemplary aspect of the invention.

Referring now to FIGS. 1-2, photodiagnostic and photodynamic therapeutic device 10 is an exemplary aspect of the present invention. Device 10 includes a diagnostic component 200 for optical detection of lesions, a treatment component 300 for treatment of lesions, and a control component 400 to control diagnostic component 200 and treatment component 300.

Figure 3:
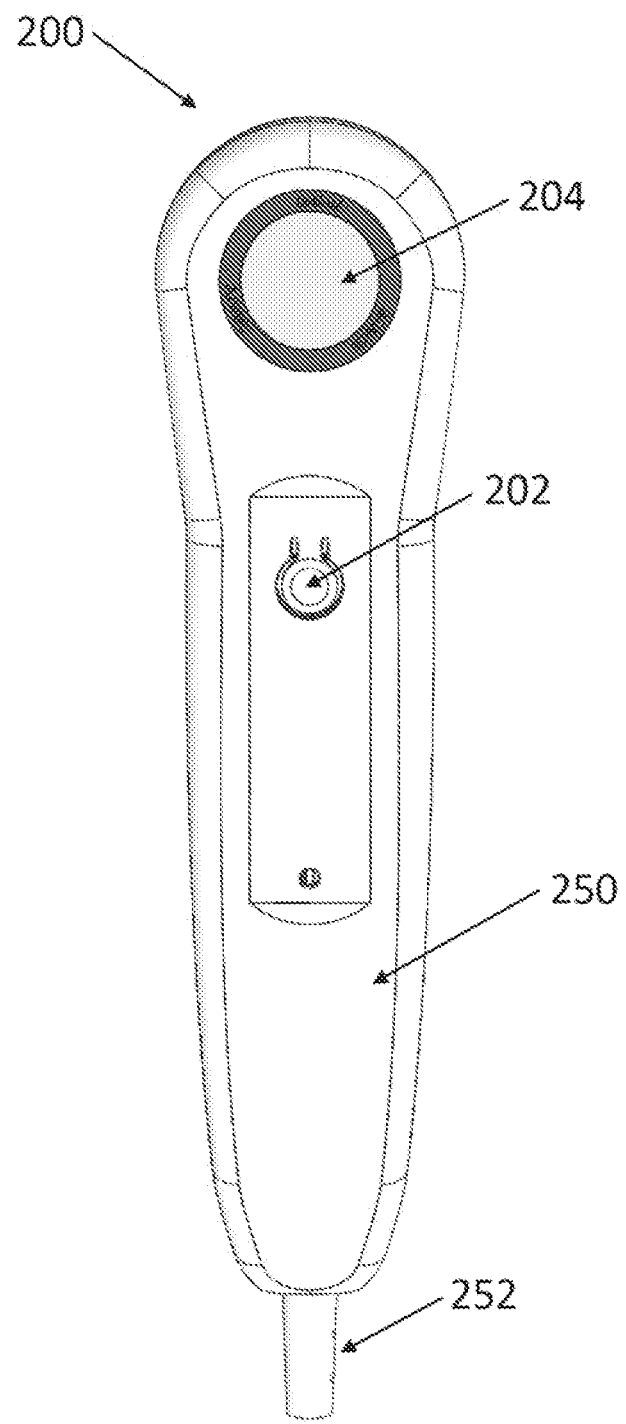
FIG. 3 is a perspective view of a photodiagnostic component of the photodiagnostic and photodynamic therapeutic device, in accordance with an exemplary aspect of the invention.
Figure 4:
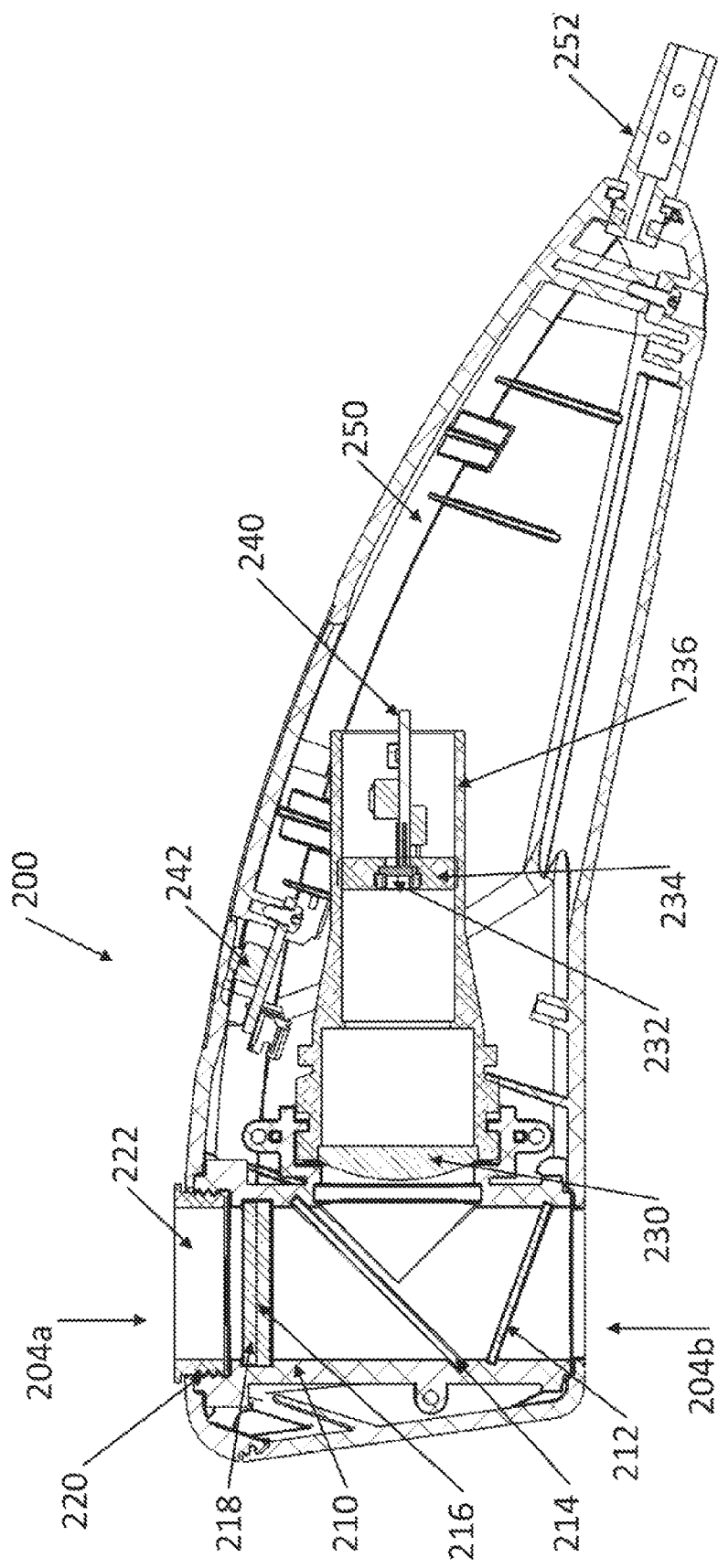
FIG. 4 is a sectional view of a photodiagnostic component of the photodiagnostic and photodynamic therapeutic device, in accordance with an exemplary aspect of the invention.
Figure 5:
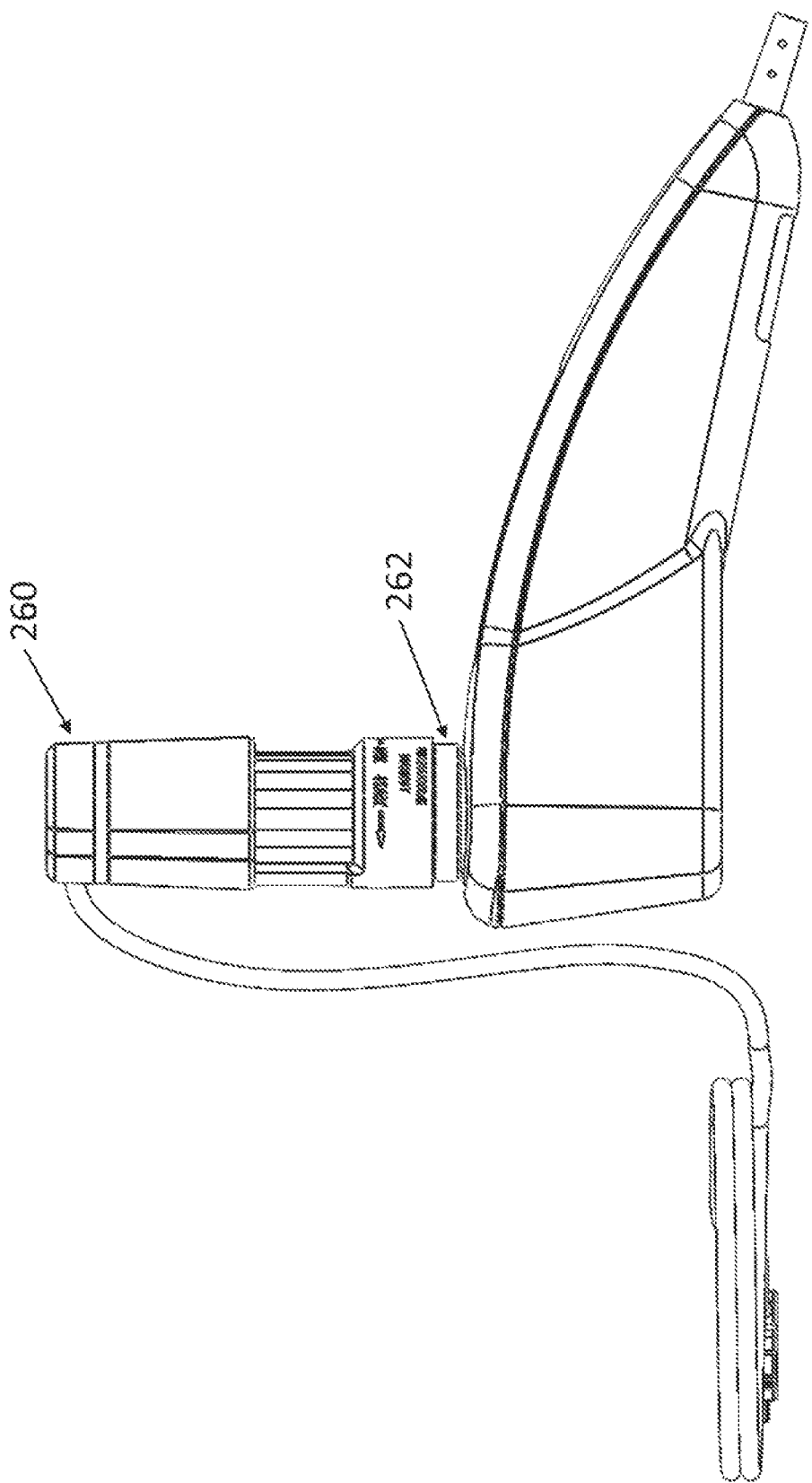
FIG. 5 is a perspective view of a of a photodiagnostic component of the photodiagnostic and photodynamic therapeutic device, in accordance with an alternate aspect of the disclosure.
Figure 6:
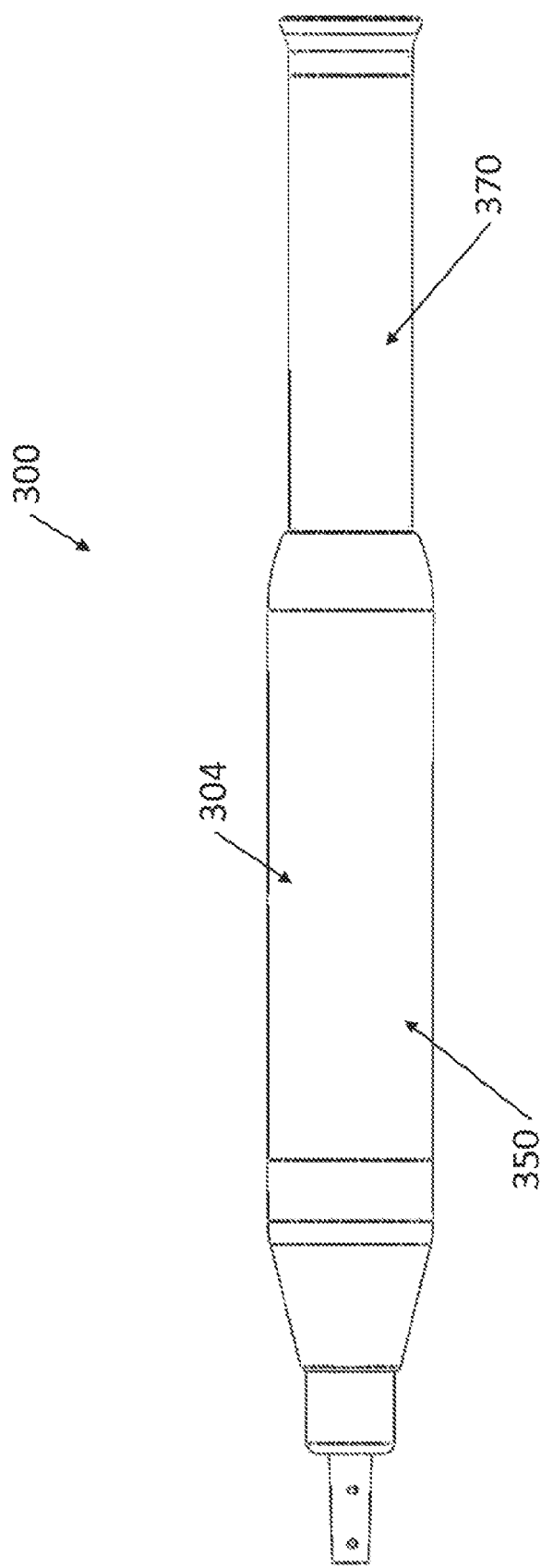
FIG. 6 is a perspective view of a photodynamic treatment component of the photodiagnostic and photodynamic therapeutic device, in accordance with an exemplary aspect of the invention.
Figure 7:
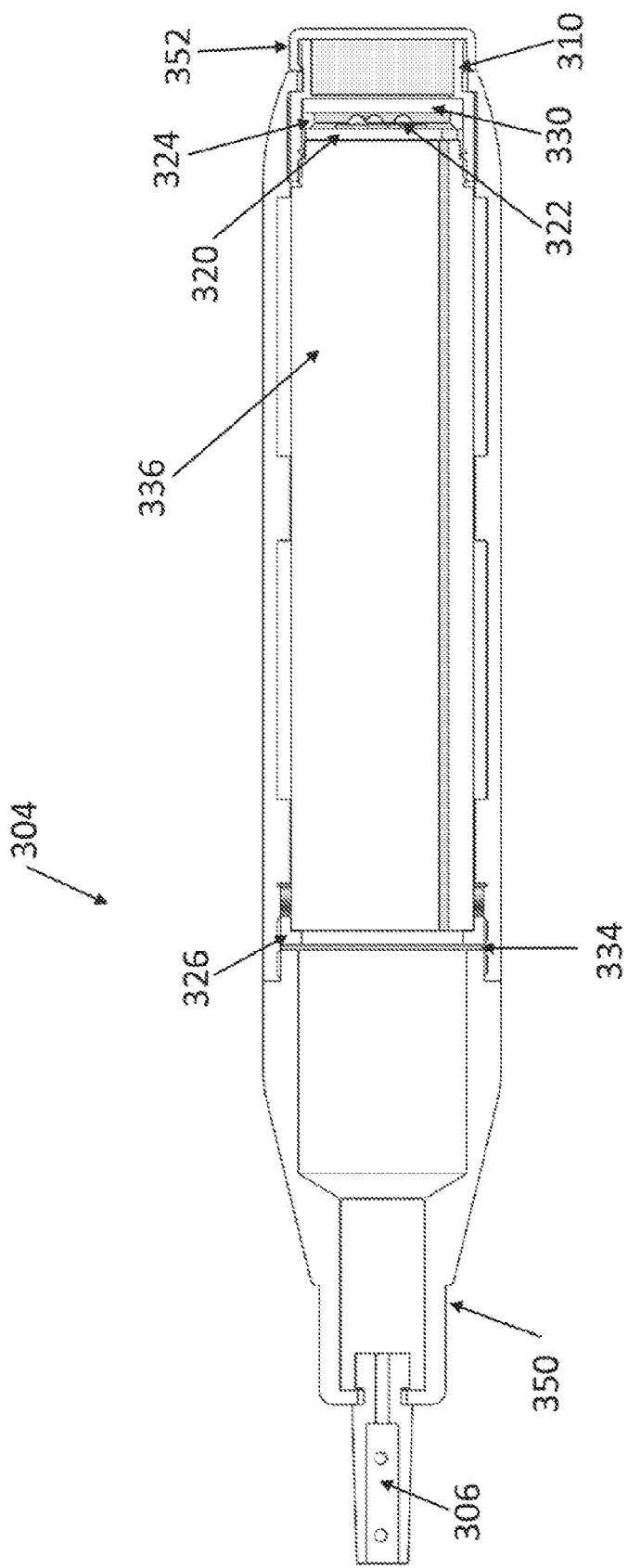
FIG. 7 is a sectional view of a portion of a photodynamic treatment component of the photodiagnostic and photodynamic therapeutic device, in accordance with an exemplary aspect of the invention.
Figure 8:
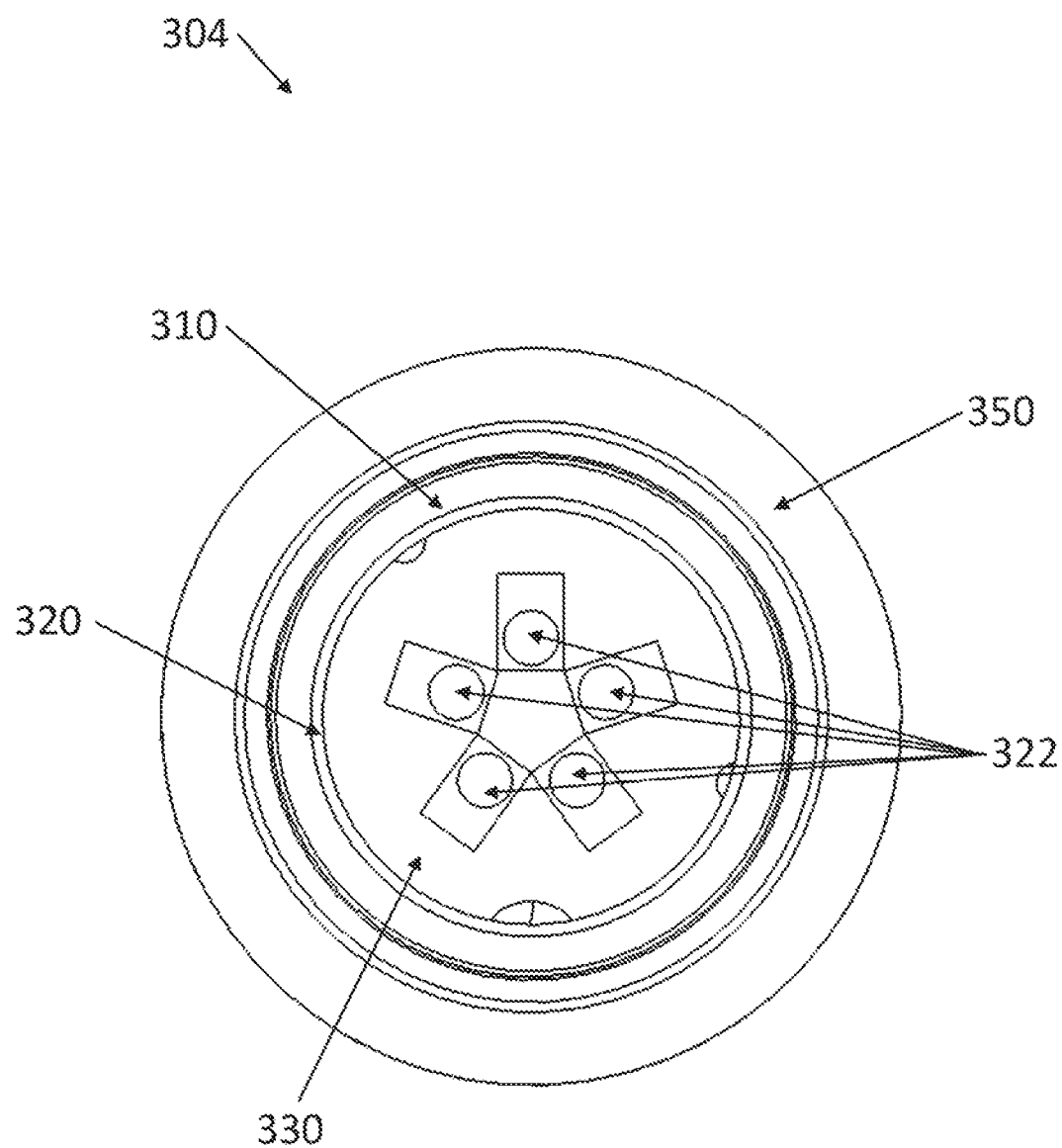
FIG. 8 is a perspective view of a portion of a photodynamic treatment component of the photodiagnostic and photodynamic therapeutic device, in accordance with an exemplary aspect of the invention.
Figure 9:
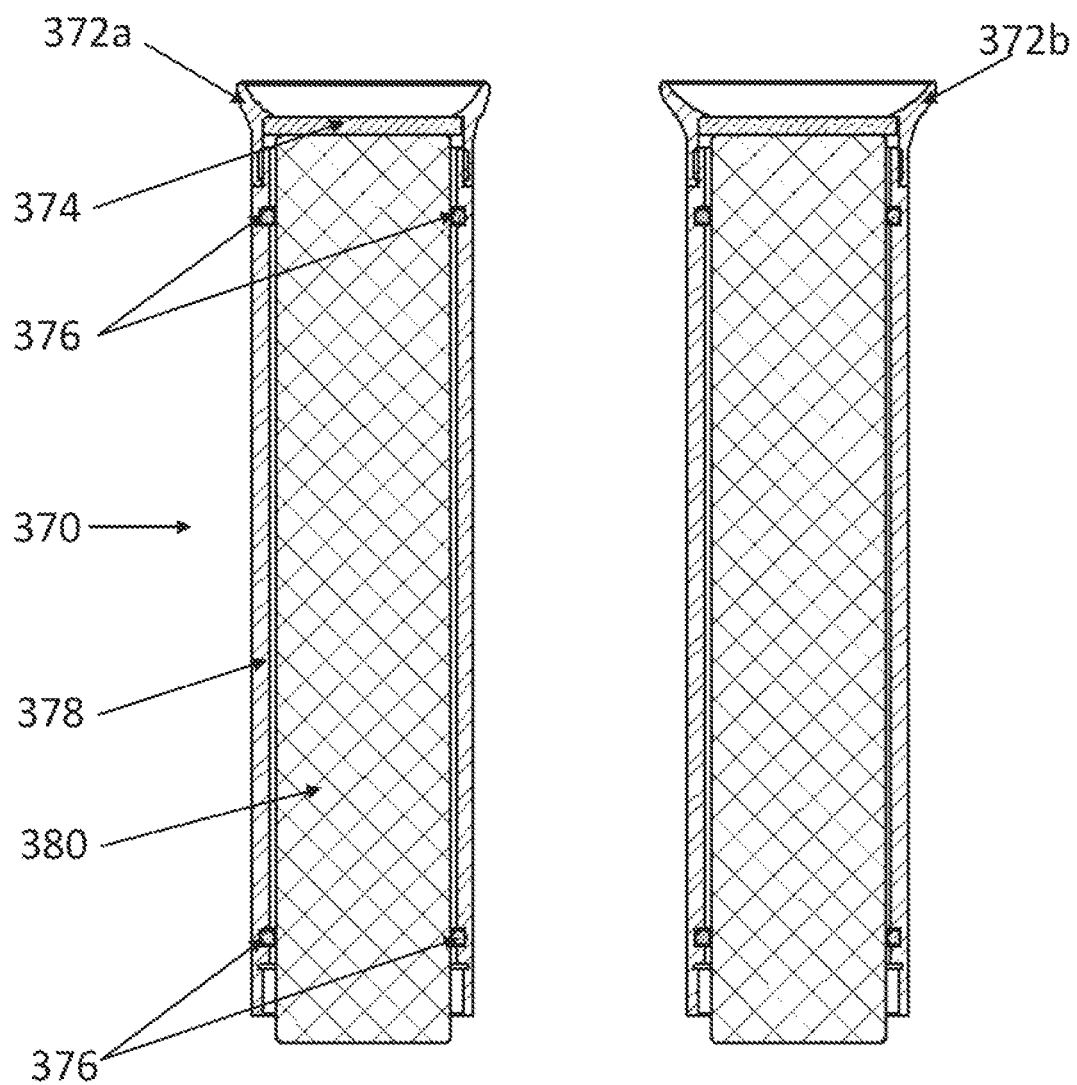
FIG. 9 is a sectional view of a portion of a photodynamic treatment component of the photodiagnostic and photodynamic therapeutic device, in accordance with an exemplary aspect of the invention.

As shown in FIGS. 3-5, diagnostic component 200 includes a series of lenses and filters to allow a medical professional to detect lesions and abnormal cells. Diagnostic component 200 is capable of detecting autofluorescence of lesions and abnormal tissue. As a result, diagnostic component 200 can be used for detection and diagnosis of abnormal tissue without having to first apply a photosensitive compound or photosensitizer. Diagnostic component 200 is contained within shell 250 and power is supplied to the system through power cord 252. Diagnostic component 200 generates a light emission and utilizes a system of optic filters that allows for the separation of a spectral region of interest from the fluorescence of the analyzed tissues.

The lenses and filters are contained within optic 204 and shell 250 of diagnostic component 200. Optic 204 is designed to allow the medical professional to look through finishing ring 222 at optic end 204a while facing optic end 204b towards the affected area of the patient. Optical support 210 is a cylindrical cavity and provides a support base for attachment of an anti-reflective filter 212, a dichroic filter 214, a notch filter 216, and a high pass filter 218. Optic 204 also includes a ring 220 to provide a base for finishing ring 222 or adapter ring 262. Ring 220 can be attached to finishing ring 222 or adapter ring 262 via a threaded engagement, an interference engagement, or other suitable attachment. Finishing ring 222 provides a window for a medical professional through which to view the tissue fluorescence with the naked eye. Alternatively, photographic camera 260 can be used to view and record the tissue fluorescence. Photographic camera 260 attaches to diagnostic component 200 using adapter ring 262. Photographic camera 260 attaches to adapter ring 262 via a threaded engagement, an interference engagement, or other suitable attachment.

The light for detection and diagnosis of abnormal tissue is generated by laser diode 232. Laser diode 232 provides a parallel beam of excitation light sufficient to access a patient's cervical tissue through the vagina. In addition, laser induced tissue fluorescence is cleaner than that of other light sources allowing diagnostic component 200 to detect autofluorescence of the tissue without having to first apply a photosensitizer to the tissue. Laser diode 232 provides a single wavelength, which allows for better selectivity in viewing the fluorescence of abnormal tissue and in viewing the formation of porphyrin. In one aspect of the invention, diagnostic component 200 utilizes a single laser diode 232 that emits light at a single wavelength. In an alternate aspect of the invention, diagnostic component 200 can include additional laser diodes to generate and provide additional light wavelengths.

Collimator lens 230 collects the light generated by laser diode 232 and collimates the light beam, generating uniformity and defining the dimension of the illumination. In one aspect of the invention, collimator lens 230 is a single lens. In an alternate aspect of the invention, collimator lens 230 includes a system of two telescoping lenses to collect the light generated by laser diode 232. In an alternate aspect of the invention, collimator lens 230 may include additional lenses to define an appropriate dimension and size of illumination.

Focus adjustment ring 234 can be low intensity and allows for an emission of light at a wavelength ranging from approximately 400 nm to approximately 450 nm. In alternate aspects of the invention, photodiagnostic component 200 can provide an emission of light at a wavelength ranging from approximately 400 nm to approximately 420 nm; approximately 400 nm to approximately 415 nm; approximately 405 nm to approximately 415 nm; e.g. 405 nm, 410 nm, 415 nm, 420 nm, 425 nm, 430 nm, 435 nm, 440 nm, 445 nm, or 450 nm. In an alternate aspect of the invention, photodiagnostic component 200 can provide an emission of light at a wavelength of approximately 418 nm. As discussed above, one or more additional laser diode can be provided to generate one or more additional light emission wavelength. In one aspect of the invention, diagnostic component 200 generates a fixed light intensity. In an alternate aspect of the invention, diagnostic component 200 can generate a continuous variation of light intensities ranging from approximately 0 mW/cm² to approximately 100 mW/cm², based on the operating range of laser diode 232. In an alternate aspect of the invention, diagnostic component 200 generates a continuous variation of light intensities ranging from approximately 15 mW/cm² to approximately 24 mW/cm². Particular light intensities for diagnostic component 200 can also be pre-programmed into control panel 408. For example, a user may be able to select from a light intensity of approximately 10 mW/cm² to approximately 30 mW/cm², e.g., approximately 15 mW/cm², approximately 20 mW/cm², approximately 25 mW/cm², or approximately 30 mW/cm². Varying the light intensity of diagnostic component 200 allows the medical professional to better see the details of the analyzed tissue. The ability to vary the light intensity also allows the medical professional to account for the varying cervix tonalities that exist among different patients and effectively allows the medical professional to control the contrast of the tissue fluorescence image seen through diagnostic component 200.

Heat dissipation system 236 surrounds laser diode 232 and prevents laser diode 232 from overheating. Heat dissipation system 236 is designed to increase the surface area in contact with the air surrounding laser diode 232, thus cooling the system. In one aspect of the invention, heat dissipation system 236 is made of metal, e.g. aluminum, or other material suitable for the transfer of thermal energy.

The excitation light leaving collimator lens 230 reflects from dichroic filter 214 towards the patient and the tissue to be analyzed. Dichroic filter 214 also protects the optic system from dust and dirt and reduces losses in the transmission of ultraviolet light. Notch filter 216 reflects the excitation light reflected by the analyzed tissue and permits transmission of the fluorescent light. High pass filter 218 allows for transmission of the fluorescence signal (red and green) and blocks yellow illumination. Support 210 also blocks ultraviolet light and allows for the transmission of fluorescence. This filter system allows for the separation of a spectral region of interest from the fluorescence of the analyzed tissues so that a medical professional can view and analyze the tissue fluorescence.

Power button 202 is located on diagnostic component shell 250 and is connected to a circuit board 242 which controls the activation of the laser diode 232. Laser diode 232 is also connected to a circuit board 240 which in turn is connected to circuit board 242. Power is supplied to diagnostic component 200 through power cord 252.

Referring now to FIGS. 6-9, treatment component 300 utilizes high intensity LEDs to treat a patient's affected area. Treatment component 300 includes light component 304 and guiding sleeve 370. When not in use, end cap 352 is attached to light component shell 350 and covers the distal end of light component 304. In one aspect of the invention, end cap 352 contains interior threads for a threaded engagement to shell 350. In an alternate aspect of the invention, end cap 352 can also be attached to shell 350 by an interference engagement or other suitable attachment.

High-intensity LEDs 322 are located on core metal plate 320 at the distal end of light component 304. Core metal plate 320 allows for the high-intensity LEDs 322 to be distributed circularly in light component 304 and to have an emission of a specified wavelength or range of wavelengths corresponding to the absorption spectrum of one or more photosensitizers in a range of approximately 400 nm to approximately 820 nm, e.g. approximately 410 nm; approximately 440 nm; approximately 447 nm; approximately 456 nm; approximately 480 nm; approximately 505 nm; approximately 525 nm; approximately 540 nm; approximately 580 nm; approximately 625 nm; approximately 630 nm; approximately 635 nm; approximately 650 nm; approximately 652 nm; approximately 653 nm; approximately 660 nm; approximately 664 nm; approximately 665 nm; approximately 670 nm; approximately 675 nm; approximately 685 nm; approximately 690 nm; approximately 732 nm; approximately 735 nm; approximately 762 nm; from approximately 615 nm to approximately 635 nm; from approximately 660 nm to approximately 665 nm; from approximately 660 nm to approximately 700 nm; from approximately 660 nm to approximately 710 nm; from approximately 670 nm to approximately 720 nm; from approximately 670 nm to approximately 780 nm; from approximately 780 nm to approximately 810 nm; and from approximately 780 nm to approximately 820 nm. In an alternate aspect of the invention, core metal plate 320 can contain multiple LEDs that emit light at different wavelengths. In this aspect, the medical professional can select the appropriate wavelength for a particular photosensitizer by selectively activating the appropriate LEDs.

In addition, treatment component 300 can generate a continuous variation of light intensities ranging from approximately 0 mW/cm$^2$ to approximately 250 mW/cm$^2$, based on the operating range of high-intensity LEDs 322. In an alternate aspect of the invention, treatment component 300 generates a continuous variation of light intensities ranging from approximately 40 mW/cm$^2$ to approximately 120 mW/cm$^2$. Particular light intensity and duration of treatment combinations for treatment component 300 can also be pre-programmed into control panel 408. For example, a user may be able to select from approximately 120 mW/cm$^2$ for 21 minutes, approximately 80 mW/cm$^2$ for 32 minutes, or approximately 40 mW/cm$^2$ for 63 minutes.

Protective screen 330 is located distal to core metal plate 320 and high-intensity LEDs 322 to protect the LEDs 322 from dust and dirt and other contaminates. High-intensity LEDs 322 generate a large amount of heat. Therefore, light component 304 includes heat sink 336. Heat sink 336 is designed to increase the surface area in contact with the air surrounding LEDs 322, thus cooling the system. In one aspect of the invention, heat sink 336 is made of metal, e.g. aluminum, or other material suitable for the transfer of thermal energy. Heat sink 336 can also provide electrical contact between power chord 306 and core metal plate 320.

The distal end of heat sink 336 abuts core metal plate 320 in order to dissipate the heat generated by high-intensity LEDs 322. Ring 334 and insulator ring 336 fasten and hold heat sink 336 to shell 350. Power is supplied to light component 304 through power cord 306.

When in use, end cap 352 is removed and guiding sleeve 370 is attached to light component 304 at guiding sleeve nozzle 310. Guiding sleeve 370 is composed of light guide 380, protective sleeve 378, and light protector 372. To attach guiding sleeve 370 to light component 304, light guide 380 is first inserted into guiding sleeve nozzle 310 and attached to shell 350. Next, protective sleeve 378 is provided over light guide 380 and is attached to guiding sleeve nozzle 310. Light protector 372 is then attached to the distal end of protective sleeve 378.

Guiding sleeve 370 directs the light from high-intensity LEDs 322 to the patient's affected area. Light protector 372 is attached to the distal end of guiding sleeve 370 to allow for dissemination of light on the patent's affected area. In one aspect of the invention, guiding sleeve 370 is inserted into the patient's vagina and light protector 372 surrounds the patient's cervix to allow treatment component 300 to illuminate the patient's cervix. In order to conform to patient anatomical variations of the cervix, light protector 372 can be different sizes ranging from approximately 20 mm to approximately 40 mm in diameter. In one aspect of the invention, light protector 372a is approximately 27 mm in diameter. In an alternate aspect of the invention, light protector 372b is approximately 33 mm in diameter. Light protector 372 can contact the patient's cervix.

Guiding sleeve 370 also includes a glass screen 374 to protect the device from biological contaminants and to allow for uniformity of illumination generated by high-intensity LEDs 322. In one aspect of the invention, glass screen 374 is attached at the distal end of guiding sleeve 370. In one aspect of the invention, all parts of guiding sleeve 370 are reusable and can be sterilized, for example, in an autoclave. In another aspect of the invention, guiding sleeve 370 is used with a biological barrier to protect treatment component 300, particularly guiding sleeve 370, from biological contaminants and to keep maintain a sterile environment. The biological barrier remains on guiding sleeve 370 during insertion and treatment and can be discarded after treatment. Biological barrier can be a sterile, disposable film or covet that conforms to the shape of guiding sleeve 370. Biological barrier can be plastic and can be a cylindrical shape having a closed end and an open end. Biological barrier can also be clear to allow the light emission to pass through unobstructed.

Protective sleeve 378 is the outermost surface of guiding sleeve 370 and can be made of metal. In one aspect of the invention, protective sleeve 378 is stainless steel (Inox) or aluminum. Protective sleeve 378 surrounds light guide 380. Light guide 380 can be made from glass or acrylic material. Light guide 380 channels and directs light generated from high-intensity LEDs 322 to the targeted location or area.

Rubber rings 376 are provided between light guide 380 and protective sleeve 378. Rubber rings 376 center protective sleeve 378 on light guide 380 and provide a biological barrier between the patient and light component 304.

In alternate aspects of the invention, the structure and design of guiding sleeve 370 can be modified to allow for illumination areas of varying sizes. The guiding sleeve 370 can be provided with a 27 mm or a 30 mm internal diameter to adapt to different cervical areas. In one aspect of the invention, the length of both guiding sleeve is approximately 108 mm. The illumination area provided by the guiding sleeve is 20 mm in diameter.

In one aspect of the invention, the targeted area illuminated by treatment component 300 is approximately 20 mm in diameter. This illumination area is generally sufficient to illuminate the patient's cervix. Treatment component 300 is able to focus the treatment beam of light to a well circumscribed targeted area, thus protecting adjacent normal anatomical structures.

Figure 10:
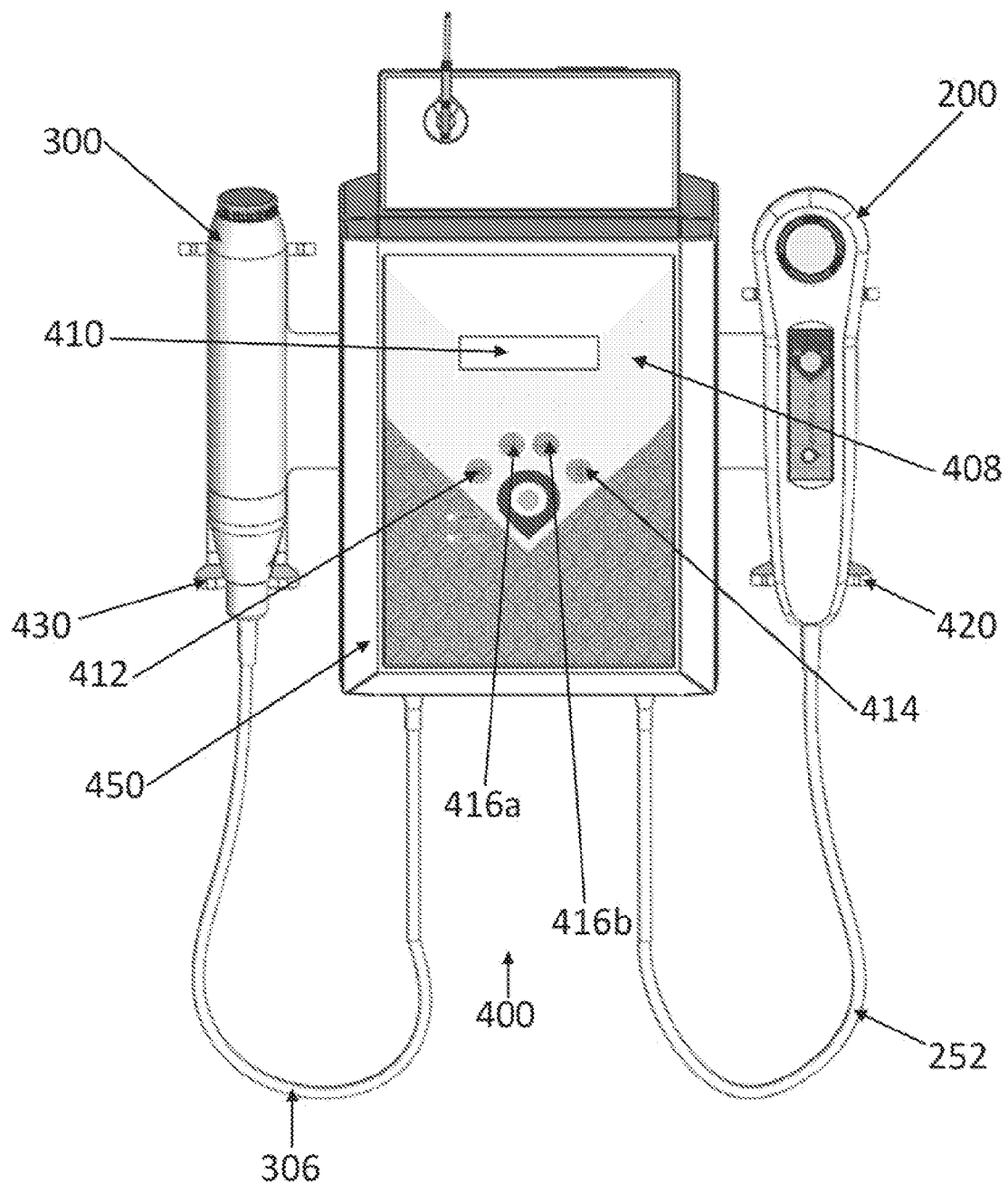
FIG. 10 is a perspective view of a photodiagnostic and photodynamic therapeutic device, in accordance with an exemplary aspect of the invention.
Figure 11:
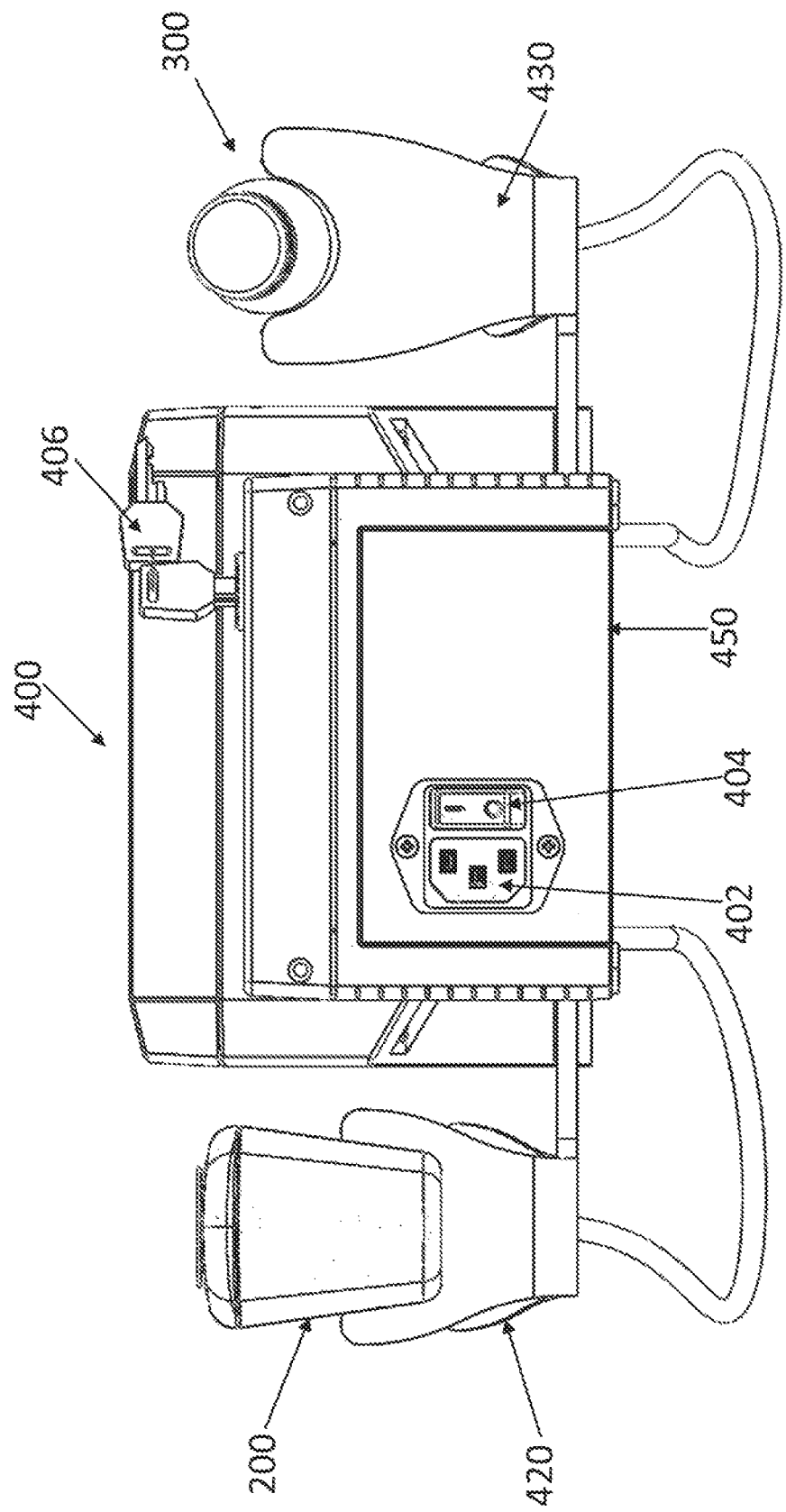
FIG. 11 is a perspective view of a photodiagnostic and photodynamic therapeutic device, in accordance with an exemplary aspect of the invention.

Referring now to FIGS. 10-11, control component 400 includes control component shell 450, power outlet 402, and master on-off switch 404. Control component 400 provides power to diagnostic component 200 and/or treatment component 300 through power cords 252 and 306, respectively. Control component 400 also includes treatment component support 430 and/or diagnostic component support 420 which retain the respective components when not in use. Control component 400 includes security key mechanism 406 which prevents unauthorized use of photodiagnostic and photodynamic therapeutic device 10. Security key mechanism 406 is a lockable power switch which prevents activation of device 10 when the security key is not in place and turned to the "on" position.

Control component 400 also includes control panel 408. Control panel 408 includes display screen 410 and operation buttons 412, 414, 416a, and 416b. Control panel 408 controls the operation of diagnostic component 200 and/or treatment component 300. Control panel 408 allows the medical professional to select for use of either diagnostic component 200 or treatment component 300.

Control panel 408 also controls the activation and light intensity of diagnostic component 200 and provides indication to the medical professional when light is being emitted by diagnostic component 200. In one aspect of the invention, control panel 408 allows the medical professional to select manually a diagnostic component 200 light intensity ranging from approximately 0 mW/cm$^2$ to approximately 100 mW/cm$^2$. In an alternate aspect of the invention, control panel 408 allows the medical professional to select manually a diagnostic component 200 light intensity ranging from approximately 15 mW/cm$^2$ to approximately 24 mW/cm$^2$. In an alternate aspect of the invention, control panel 408 can be programmed to allow the medical professional to select manually a diagnostic component 200 light intensity within a specified range of the light intensity operating range of laser diode 232. In an alternate aspect of the invention, control panel 408 provides diagnostic component 200 with fixed light intensity selection options including, for example, approximately 15 mW/cm$^2$, approximately 20 mW/cm$^2$, approximately 25 mW/cm$^2$, and approximately 30 mW/cm$^2$.

Control panel 408 also allows the medical professional to select the desired dose of light energy to be delivered by treatment component 300. Treatment component 300 has two operating modes: "manual" and "protocol." The manual mode allows the medical professional to select the level of light intensity up to a maximum of approximately 250 mW/cm$^2$. Therefore, control panel 408 allows the medical professional to select manually a treatment component 300 light intensity ranging from approximately 0 mW/cm$^2$ to approximately 250 mW/cm$^2$, the operating range of high-intensity LEDs 322 of treatment component 300. In an alternate aspect of the invention, control panel 408 allows the medical professional to select manually a treatment component 300 light intensity ranging from approximately 40 mW/cm$^2$ to approximately 120 mW/cm$^2$. In an alternate aspect of the invention, control panel 408 can be programmed to allow the medical professional to select manually a treatment component 300 light intensity within a specified range of the light intensity operating range of high-intensity LEDs 322.

The manual mode also allows a medical professional to select an appropriate duration of treatment for a selected light intensity. Thus, the manual mode allows for greater flexibility and customization of the clinical treatment. Protocol mode provides predefined options of frequently used light intensity and duration of treatment combinations that are preprogrammed into control panel 408. For example, approximately 120 mW/cm$^2$ for 21 minutes, approximately 80 mW/cm$^2$ for 32 minutes, or approximately 40 mW/cm$^2$ for 63 minutes. In protocol mode, each treatment combination results in the same dose of light energy, approximately 150 J/cm$^2$, to the patient. However, other doses may be appropriate as one of ordinary skill in the art can easily determine.

Figure 12:
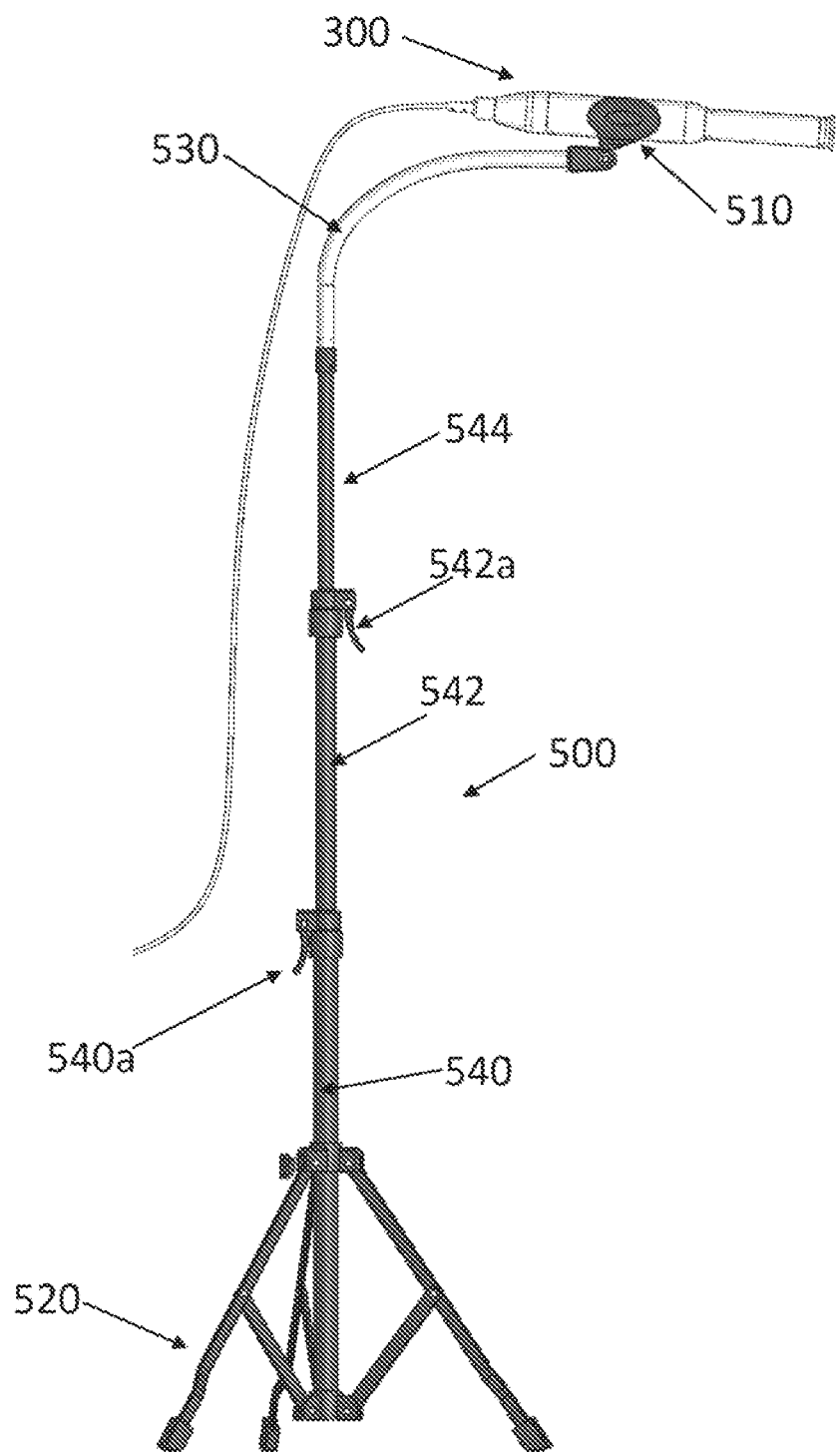
FIG. 12 is a front view of a support for a photodynamic treatment component of a photodiagnostic and photodynamic therapeutic device, in accordance with an exemplary aspect of the invention.

Referring now to FIG. 12, adjustable support 500 allows for positioning of treatment component 300 to allow for accurately positioning the light to the cervical area during treatment. Support 500 includes a coupling 510 to attach to treatment component 300. Support 500 includes foldable legs 520, telescopic tubes 540, 542, and 544, and adjustment locks 540a and 542a to regulate the height and position of treatment component 300. Support 500 also includes flexible rod 530 for fine adjustments to the positioning of treatment component 300. In one aspect of the invention, support 500 allows for a variable height ranging from approximately 80 cm to approximately 140 cm.

Figure 16:
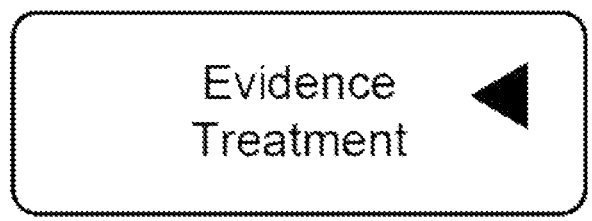
FIG. 16 depicts a user interface, in accordance with an exemplary aspect of the invention.
Figure 18:
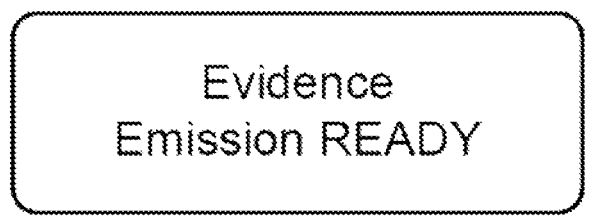
FIG. 18 depicts a user interface, in accordance with an exemplary aspect of the invention.
Figure 19:
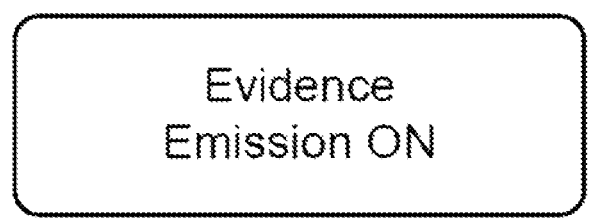
FIG. 19 depicts a user interface, in accordance with an exemplary aspect of the invention.
Figure 20:
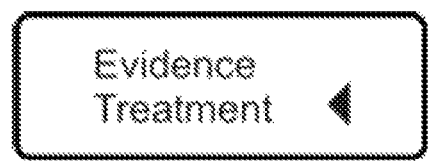
FIG. 20 depicts a user interface, in accordance with an exemplary aspect of the invention.

Operation of the diagnostic component 200 will now be described. FIGS. 16-19 depict information displayed on display screen 410 during operation of diagnostic component 200. In one aspect of the invention, control component 400 controls diagnostic component 200. In another aspect of the invention, control component 400 controls treatment component 300. In an alternate aspect of the invention, control component 400 controls diagnostic component 200 and/or treatment component 300. In this aspect, as shown in FIGS. 16 and 20, the medical professional can select from the "evidence" or "detection" or "diagnostic" option to operate diagnostic component 200 or the "treatment" option to operate treatment component 300. The selection is made using one or more of operation buttons 412, 414, 416a, and 416b.

Figure 17:
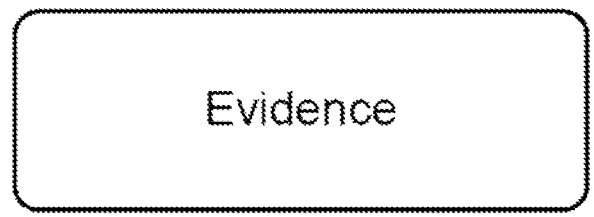
FIG. 17 depicts a user interface, in accordance with an exemplary aspect of the invention.

If "evidence" is selected, screen 410 indicates that such selection has been made, as shown in FIG. 17. The medical professional then presses operation button 414 on control component 400 which prompts display screen 410 to display that diagnostic component 200 is ready for emission of light, as shown in FIG. 18. Next, to begin emission of light, the medical professional presses power button 202 on diagnostic component 200. Display screen 410 then indicates that emission of light has initiated, as shown in FIG. 19. In one aspect of the invention, the light intensity on diagnostic component 200 is fixed. In an alternate aspect of the invention, control panel 408 allows the medical professional to select a diagnostic component 200 light intensity within the operating range of laser diode 232 ranging from approximately 0 to approximately 100 mW/cm$^2$. In an alternate aspect of the invention, control panel 408 allows the medical professional to select a diagnostic component 200 light intensity ranging from approximately 15 mW/cm$^2$ to approximately 24 mW/cm$^2$. In a further aspect of the invention, control panel 408 provides diagnostic component 200 light intensity selection options including, for example, approximately 15 mW/cm$^2$, approximately 20 mW/cm$^2$, approximately 25 mW/cm$^2$, and approximately 30 mW/cm$^2$. In a further aspect of the invention where diagnostic component 200 includes multiple laser diodes, control panel 408 can provide light emission wavelength selection options.

Figure 13:
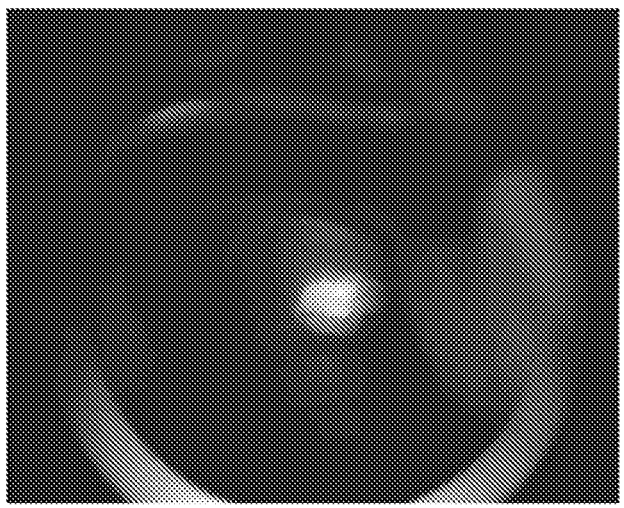
FIG. 13 is an image representing tissue autofluorescence as shown by a photodynamic treatment component of the photodiagnostic and photodynamic therapeutic device, in accordance with an exemplary aspect of the invention.

Diagnostic component 200 allows a medical professional to noninvasively detect existing differences between healthy tissue and abnormal tissue. Diagnostic component 200 can detect autofluorescence of the abnormal tissue, fluorescence of the abnormal tissue after the photosensitizer is applied, or fluorescence of the abnormal tissue after treatment with treatment component 300. An example of tissue autofluorescence of Grade II cervical dysplasia (CIN II) as detected by diagnostic component 200 is provided in FIG. 13. An example of tissue fluorescence of Grade I cervical dysplasia (CIN I) after use of a photosensitizer as detected by diagnostic component 200 is provided in FIG. 14. An example of tissue fluorescence of Grade I cervical dysplasia (CIN I) after treatment with treatment component 300 as detected by diagnostic component 200 is provided in FIG. 15.

Figure 21:
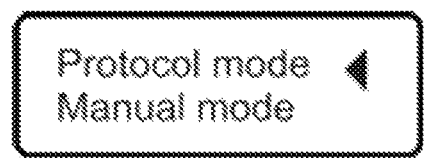
FIG. 21 depicts a user interface, in accordance with an exemplary aspect of the invention.
Figure 22:
FIG. 22 depicts a user interface, in accordance with an exemplary aspect of the invention.
Figure 23:
FIG. 23 depicts a user interface, in accordance with an exemplary aspect of the invention.
Figure 24:
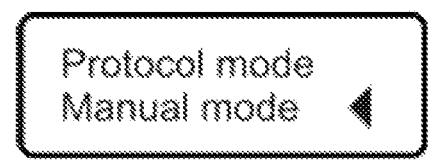
FIG. 24 depicts a user interface, in accordance with an exemplary aspect of the invention.

Operation of treatment component 300 will now be described. FIGS. 20-26 depict information displayed on display screen 410 during operation of treatment component 300. As shown FIGS. 16 and 20, the medical professional first selects from the evidence option to operate diagnostic component 200 or the treatment option to operate treatment component 300. After treatment is selected, the medical professional must choose between one of two operating modes: "protocol" mode or "manual" mode as shown in FIGS. 21 and 24. Protocol mode provides predefined options of frequently used treatment combinations for a fixed dose of approximately 150 J/cm$^2$. Manual mode allows a medical professional to select an appropriate dose of light energy including an appropriate duration of treatment for a particular selected light intensity. Thus, the manual mode allows for greater flexibility and customization of the clinical treatment.

In an aspect of the invention, protocol mode is programmed to provide the medical professional with three predetermined options: P1—approximately 120 mW/cm$^2$ for 21 minutes; P2—approximately 80 mW/cm$^2$ for 32 minutes; or P3—approximately 40 mW/cm$^2$ for 63 minutes. Each option provides the same dose of light energy, approximately 150 J/cm$^2$. The medical professional selects the appropriate option and presses operation button 414 on control component 400 to activate the high-intensity LEDs 322 on treatment component 300. After activation, display screen 410 displays the duration of treatment in a countdown format, as shown in FIG. 23.

In an alternate aspect of the invention, treatment component 300 can include a power button placed on shell 350. After the medical professional selects the appropriate option and presses operation button 414, control panel 408 displays that treatment component 300 is ready for emission of light. Next, to begin emission of light, the medical professional presses the power button on treatment component 300. Display screen 410 then indicates that emission of light has initiated.

Figure 25:
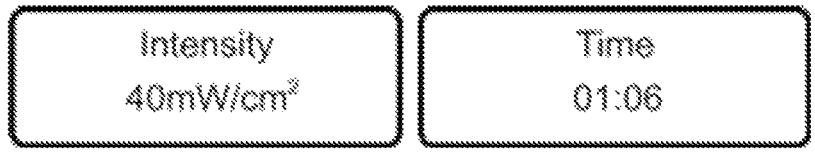
FIG. 25 depicts a user interface, in accordance with an exemplary aspect of the invention.
Figure 26:
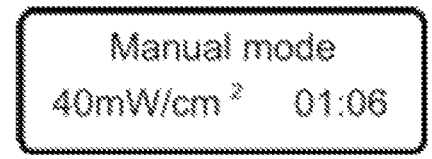
FIG. 26 depicts a user interface, in accordance with an exemplary aspect of the invention.

In an aspect of the invention, manual mode is programmed to provide the medical professional with a selection from 5 intensity levels: approximately 40 mW/cm$^2$, approximately 60 mW/cm$^2$, approximately 80 mW/cm$^2$, approximately 100 mW/cm$^2$, and approximately 120 mW/cm$^2$. In an alternate aspect of the invention, the medical professional is able to continuously vary the light intensity from approximately 0 mW/cm$^2$ to approximately 250 mW/cm$^2$ as appropriate, within the operating range of high-intensity LEDs 322. The medical professional is also permitted to vary the duration of treatment from approximately 1 to approximately 90 minutes at approximately 1 minute intervals to allow for a dose of light energy selected by the medical professional. The intensity and time selections are presented on display screen 410, as shown in FIG. 25. The medical professional uses arrow buttons 416a and 416b and select button 414 to make the appropriate intensity and duration of treatment selections.

Figure 27:
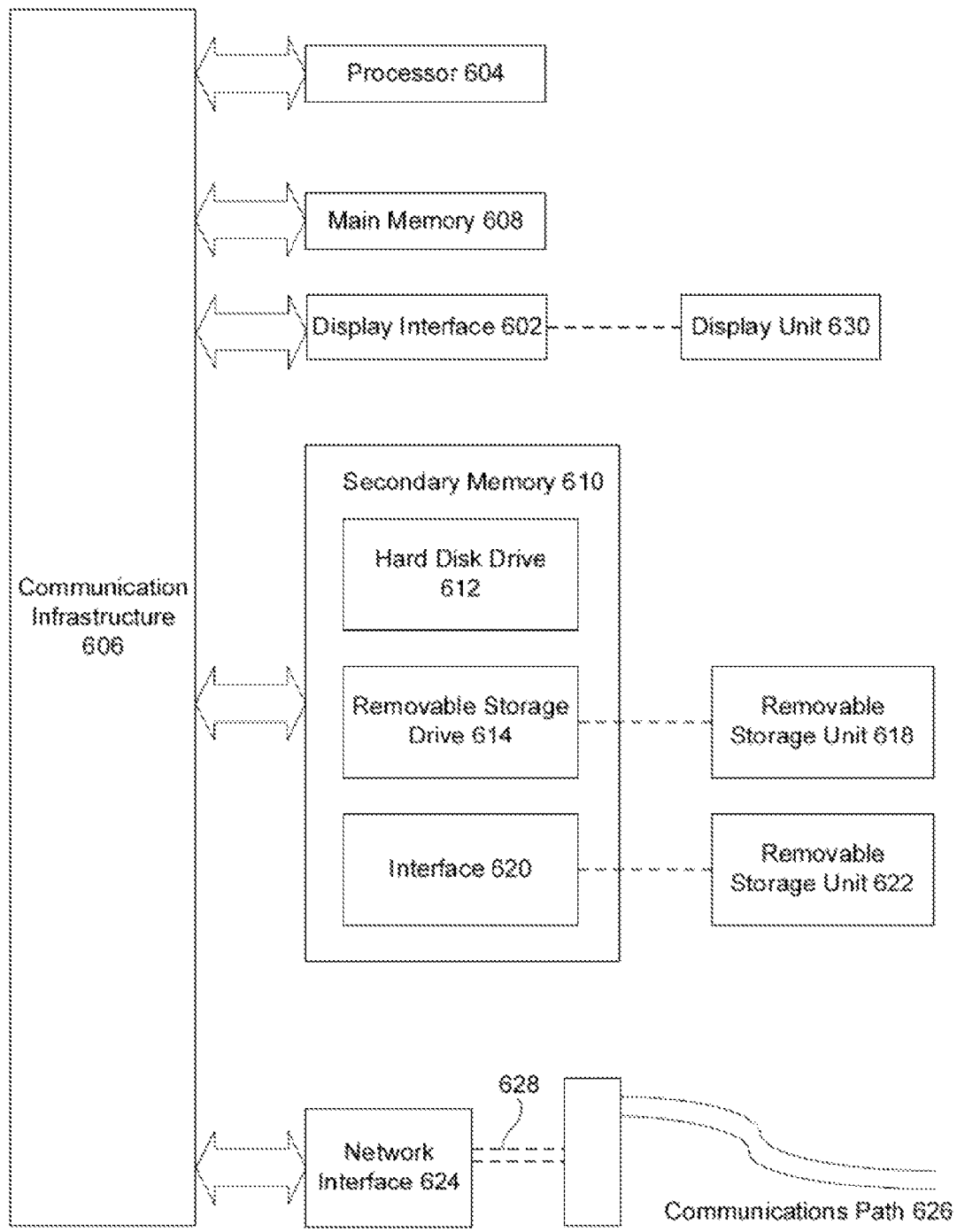
FIG. 27 depicts an example computer system in which embodiments of the present invention may be implemented.
Figure 28:
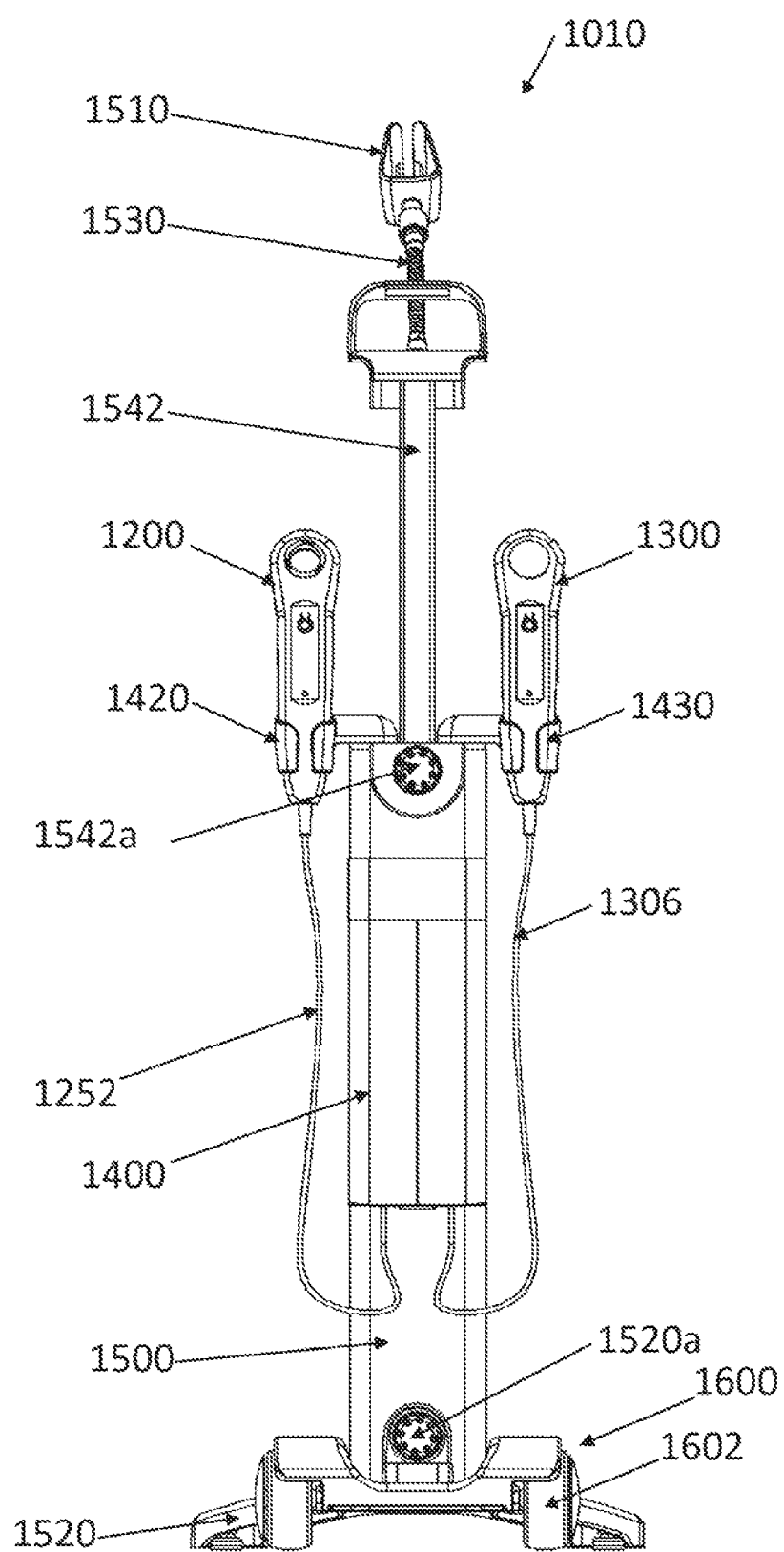
FIG. 28 is a front view of a photodiagnostic and photodynamic therapeutic device, in accordance with an exemplary aspect of the invention.
Figure 29:
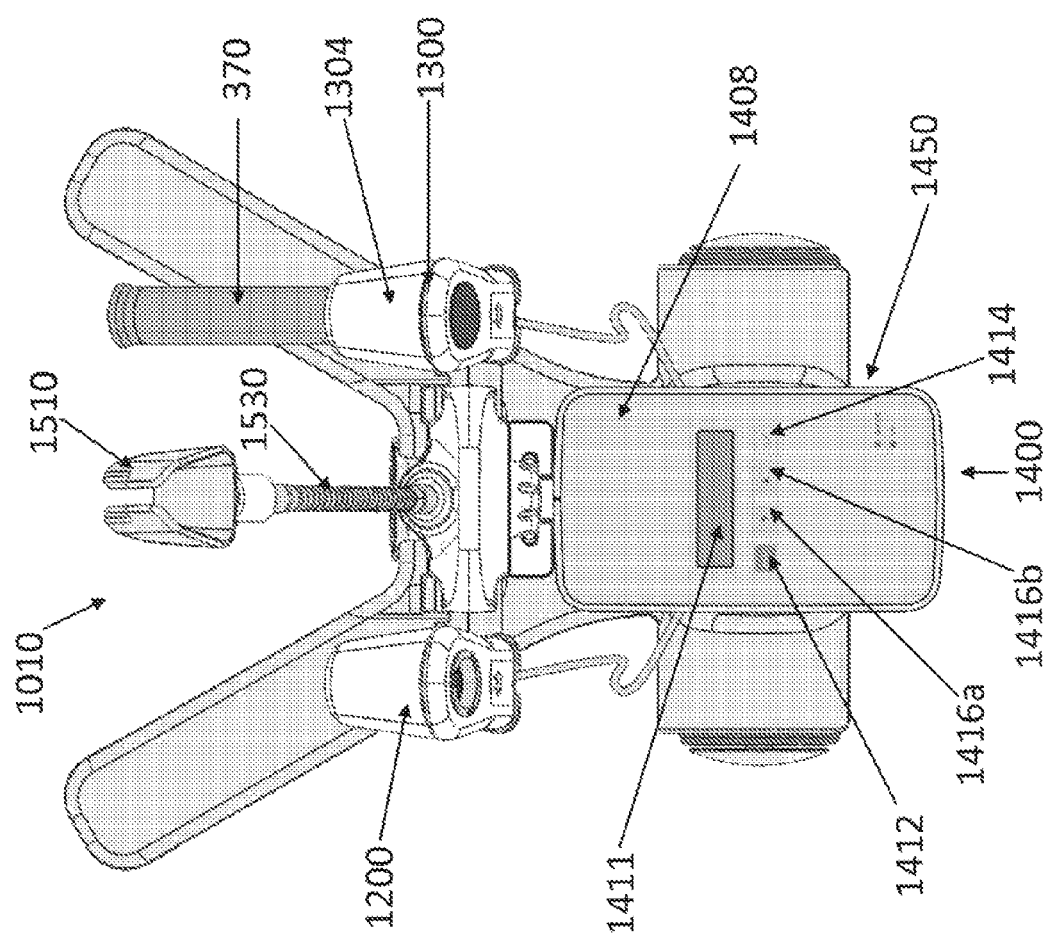
FIG. 29 is a top view of a photodiagnostic and photodynamic therapeutic device, in accordance with an exemplary aspect of the invention.
Figure 30:
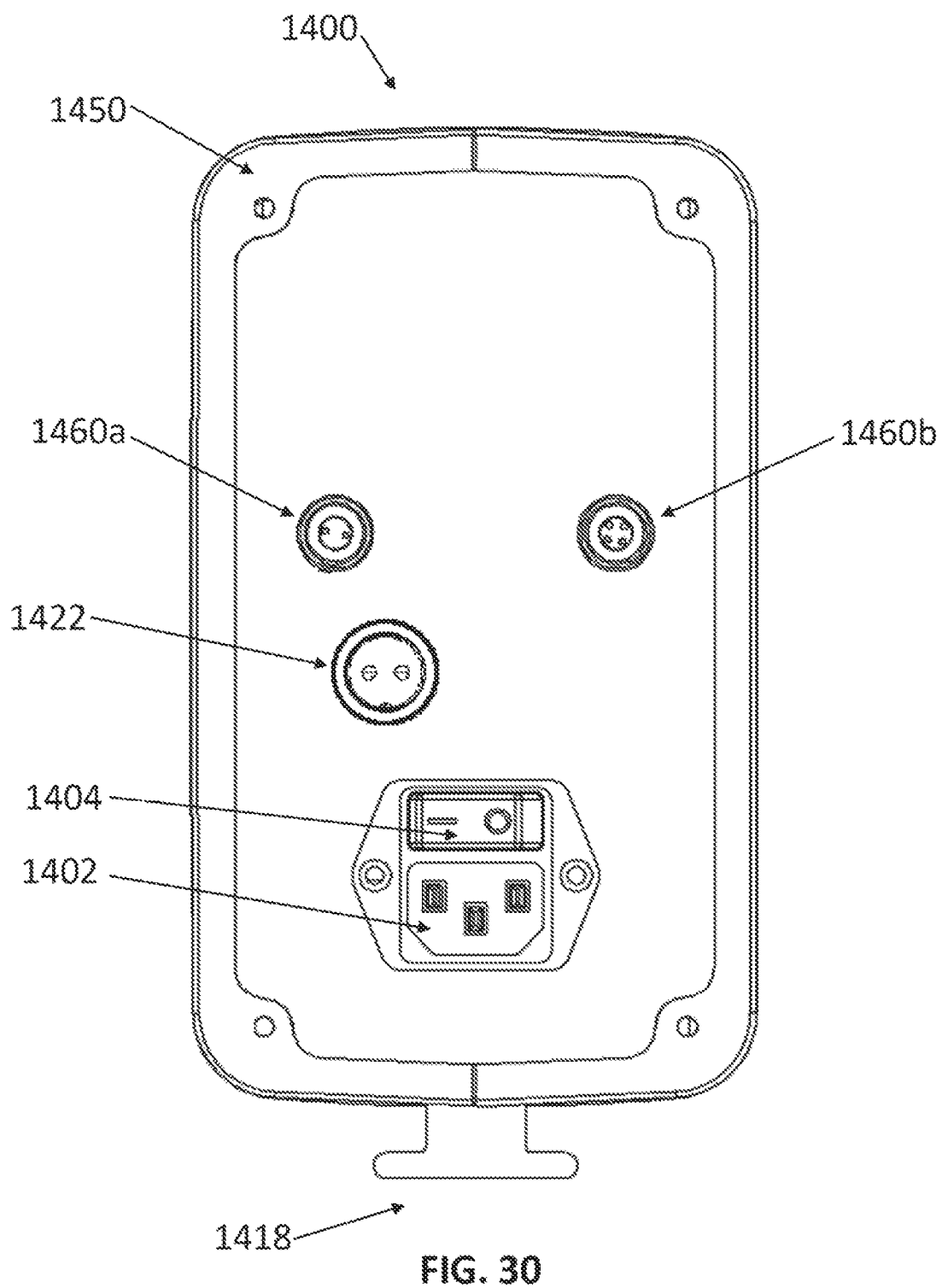
FIG. 30 is a back view of a control component of the photodiagnostic and photodynamic therapeutic device, in accordance with an exemplary aspect of the invention.
Figure 31:
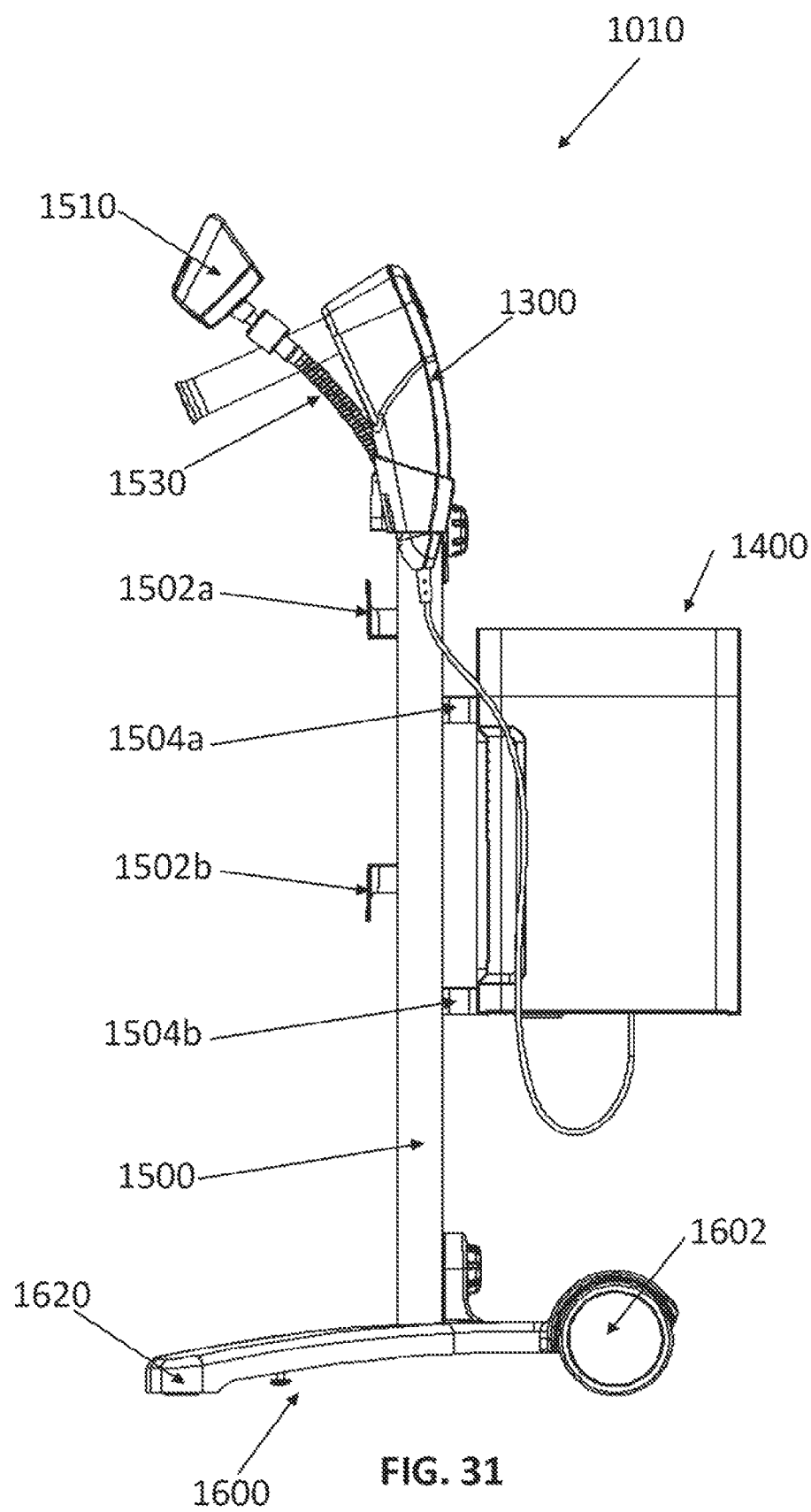
FIG. 31 is a side view of a photodiagnostic and photodynamic therapeutic device, in accordance with an exemplary aspect of the invention.
Figure 32:
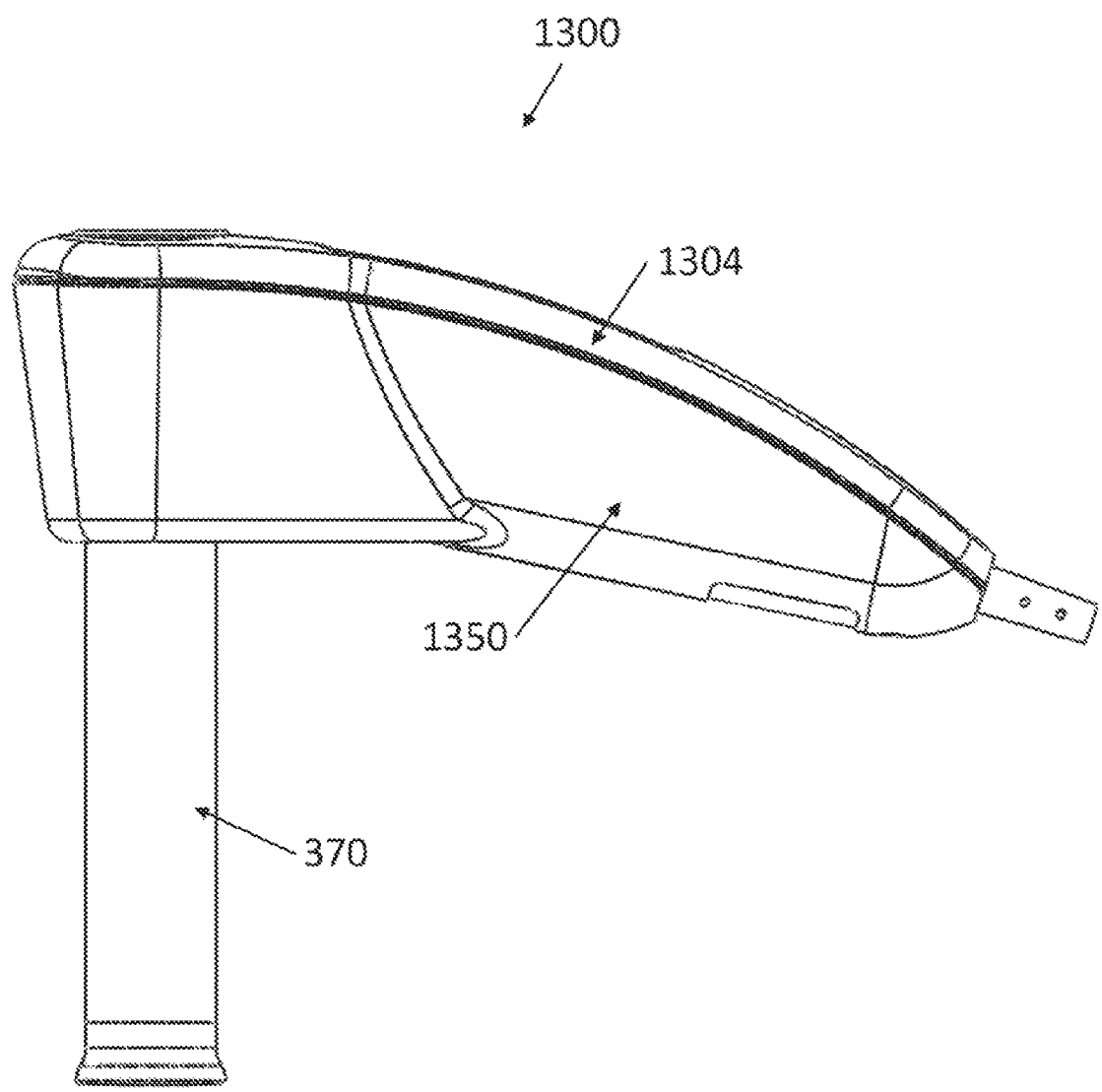
FIG. 32 is a side view of a photodynamic treatment component of the photodiagnostic and photodynamic therapeutic device, in accordance with an exemplary aspect of the invention.
Figure 33:
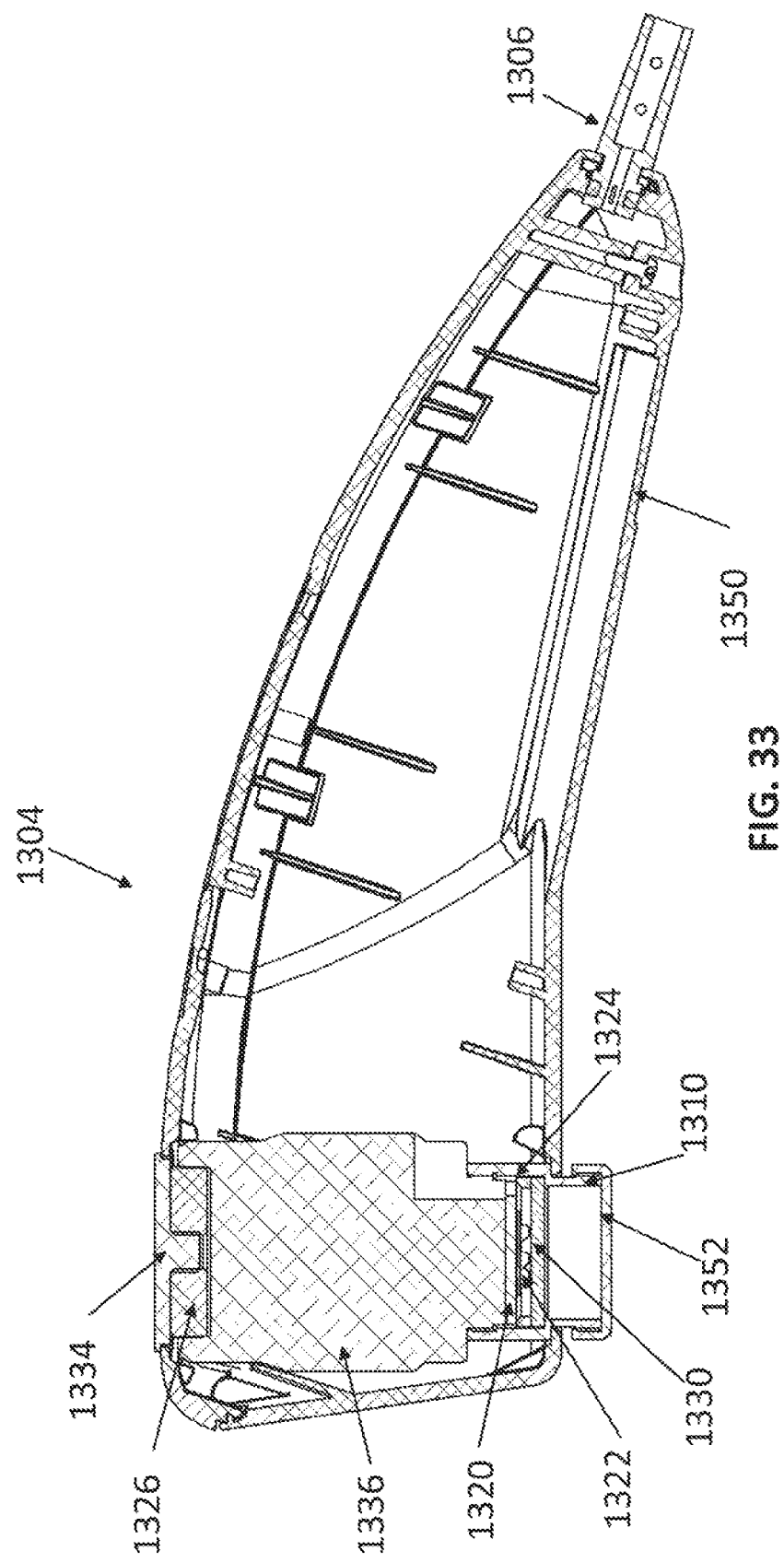
FIG. 33 is a side sectional view of a photodynamic treatment component of the photodiagnostic and photodynamic therapeutic device, in accordance with an exemplary aspect of the invention.
Figure 34:
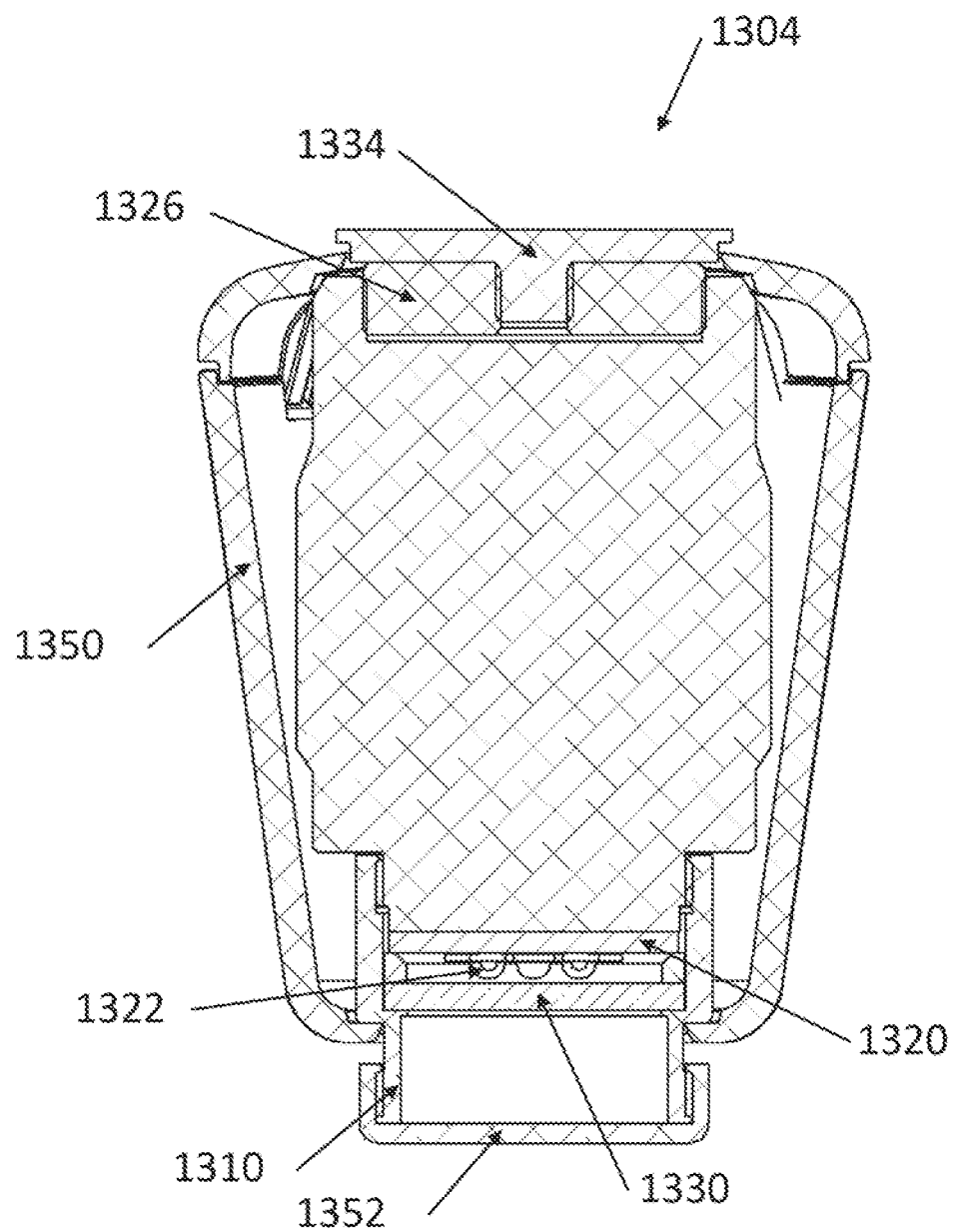
FIG. 34 is a front sectional view of a portion of a photodynamic treatment component of the photodiagnostic and photodynamic therapeutic device, in accordance with an exemplary aspect of the invention.
Figure 35:
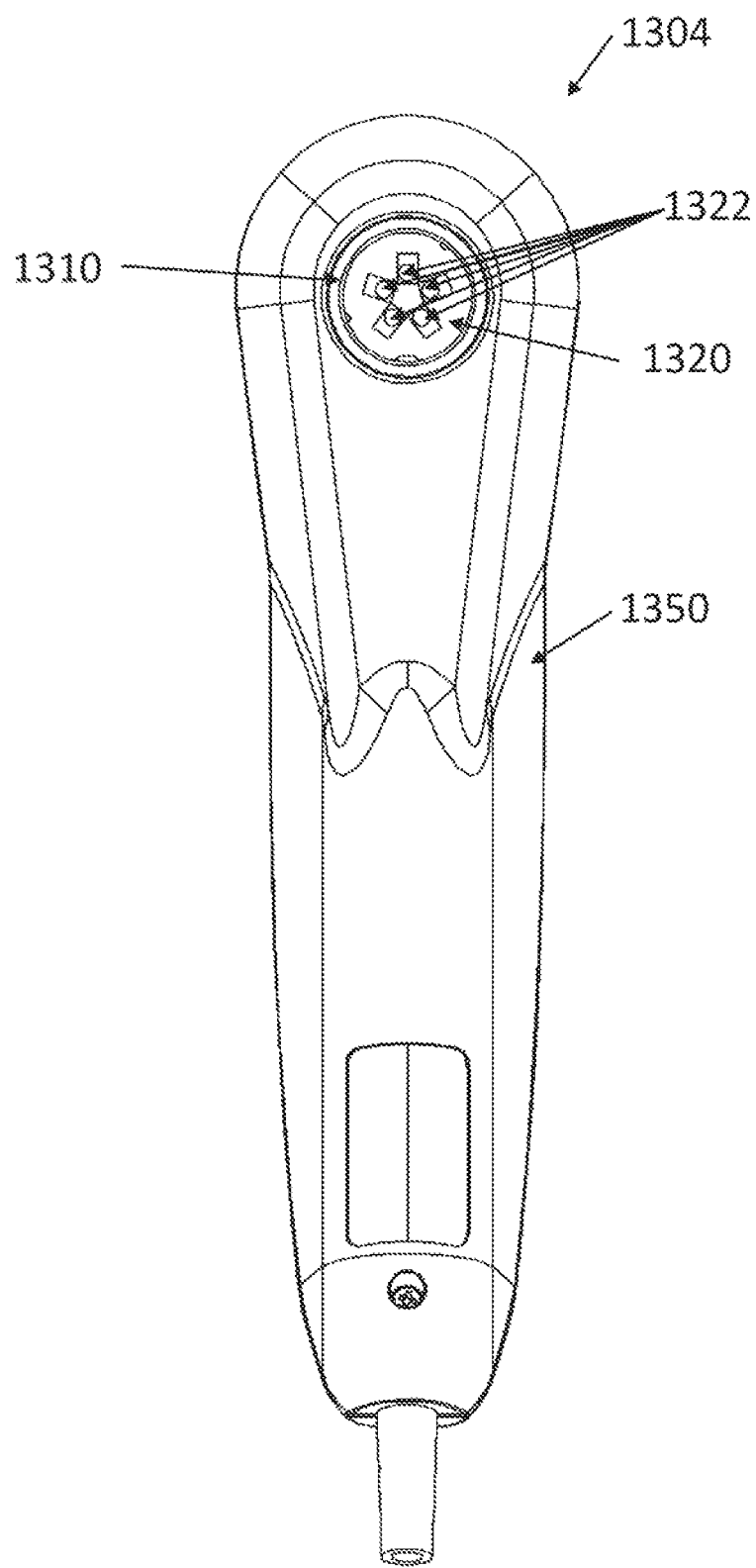
FIG. 35 is a bottom view of a portion of a photodynamic treatment component of the photodiagnostic and photodynamic therapeutic device, in accordance with an exemplary aspect of the invention.

Various aspects of control panel 408 can be implemented by software, firmware, hardware, or a combination thereof. FIG. 27 illustrates an example computer system 600 in which the present invention, or portions thereof, can be implemented as computer-readable code. Various embodiments of the invention are described in terms of this example computer system 600.

Computer system 600 includes one or more processors, such as processor 604. Processor 604 can be a special purpose or a general purpose processor. Processor 604 is connected to a communication infrastructure 606 (for example, a bus or network).

Computer system 600 also includes a main memory 608, preferably random access memory (RAM), and may also include a secondary memory 610. Secondary memory 610 may include, for example, a hard disk drive 612, a removable storage drive 614, and/or a memory stick. Removable storage drive 614 may comprise a floppy disk drive, a magnetic tape drive, an optical disk drive, a flash memory, or the like. The removable storage drive 614 reads from and/or writes to a removable storage unit 618 in a well-known manner. Removable storage unit 618 may comprise a floppy disk, magnetic tape, optical disk, etc. that is read by and written to by removable storage drive 614. As will be appreciated by persons skilled in the relevant art(s), removable storage unit 618 includes a computer usable storage medium having stored therein computer software and/or data.

In alternative implementations, secondary memory 610 may include other similar means for allowing computer programs or other instructions to be loaded into computer system 600. Such means may include, for example, a removable storage unit 622 and an interface 620. Examples of such means may include a program cartridge and cartridge interface (such as that found in video game devices), a removable memory chip (such as an EPROM, or PROM) and associated socket, and other removable storage units 622 and interfaces 620 that allow software and data to be transferred from the removable storage unit 622 to computer system 600.

Computer system 600 may also include a network interface 624. Network interface 624 allows software and data to be transferred between computer system 600 and external devices. In one aspect of the invention, an external device is an electronic patient database that records and maintains patient records. Network interface 624 may include a modem, a network interface (such as an Ethernet card), a communications port, a PCMCIA slot and card, or the like. Software and data transferred via network interface 624 are in the form of signals 628 that may be electronic, electromagnetic, optical, or other signals capable of being received by network interface 624. These signals 628 are provided to network interface 624 via a communications path 626. Communications path 626 carries signals 628 and may be implemented using wire or cable, fiber optics, a phone line, a cellular phone link, an RF link or other communications channels.

In this document, the terms "computer program medium" and "computer usable medium" are used to generally refer to media such as removable storage unit 618, removable storage unit 622, and a hard disk installed in hard disk drive 612. Signals carried over communications path 626 can also embody the logic described herein. Computer program medium and computer usable medium can also refer to memories, such as main memory 608 and secondary memory 610, which can be memory semiconductors (e.g. DRAMs, etc.). These computer program products are means for providing software to computer system 600.

Computer programs (also called computer control logic) are stored in main memory 608 and/or secondary memory 610. Computer programs may also be received via network interface 624. Such computer programs, when executed, enable computer system 600 to implement the present invention as discussed herein. In particular, the computer programs, when executed, enable processor 604 to implement the processes of the present invention, as discussed above. Accordingly, such computer programs represent controllers of the computer system 600. Where the invention is implemented using software, the software may be stored in a computer program product and loaded into computer system 600 using removable storage drive 614, interface 620, hard drive 612 or network interface 624.

The invention is also directed to computer program products comprising software stored on any computer useable medium. Such software, when executed in one or more data processing device, causes a data processing device(s) to operate as described herein. Embodiments of the invention employ any computer useable or readable medium, known now or in the future. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, MEMS, nanotechnological storage device, etc.), and communication mediums (e.g., wired and wireless communications networks, local area networks, wide area networks, intranets, etc.).

Preparation of the patient for photodynamic diagnosis and treatment will now be described. Prior to diagnosis or treatment, the patient is asked to lie down on the operating table with their legs in stirrups with necessary clothing removed.

In order to evaluate the fluorescence of the cells on the patient's cervix, the medical professional positions diagnostic component 200 in front of the patient's vagina and uses a speculum to allow access to the patient's cervix. The medical professional then begins emission of light and illuminates the patient's cervix with diagnostic component 200. The medical professional looks through optic 204 with the naked eye or utilizes camera 260 to view the tissue fluorescence of the patient's affected area. If the medical professional determines that abnormal tissue is present, the medical professional can then utilize treatment component 300 to destroy the abnormal tissue.

The medical professional evaluates the fluorescence of the cells in the affected area prior to and after photodynamic treatment using diagnostic component 200. For example, diagnostic component 200 can detect autofluorescence of abnormal tissue. In addition to detecting abnormal tissue, the medical professional can use diagnostic component 200 to measure the appropriate production of PpIX prior to treatment and to verify that the photosensitizer has been fully used after the treatment. Thus, diagnostic component 200 can be used to evaluate the effectiveness and progress of the photodynamic therapy.

Prior to using treatment component 300, a photosensitizer is applied to the patient's affected area including abnormal tissue. In one aspect of the invention, the photosensitizer is MAL. In an alternate aspect of the invention, the photosensitizer is 5-ALA. In an alternate aspect of the invention, the photosensitizer is a combination of ALA and MAL. In an alternate aspect of the invention, the photosensitizer is one or a mixture of the photosensitizers discussed above. Each photosensitizer is activated by a specific wavelength of light. Therefore, use of a different photosensitizer requires use of different LEDs in treatment component 300 in order to produce the desired wavelength. The photosensitizer is mixed into a cream for application to the patient's affected area.

After application to the patient's affect area, the photosensitizer is allowed to penetrate the affected area for a period of time as discussed above. After penetration of the photosensitizer, light component 304 is attached to guiding sleeve 370 and treatment component 300 is attached to support 500. The treatment component 300 is placed in position for treatment such that light protector 372 on guiding sleeve 370 is adjacent the patient's affected area. In one aspect of the invention, the patient's affected area can be located on the patient's cervix. To reach the cervix and the affected area, guiding sleeve 370 passes through the patient's vagina so that light protector 372 surrounds the cervix. Light component 304 remains external to the patient's body during photodynamic treatment.

After placement of treatment component 300, the medical professional selects the appropriate dose of light energy to treat the patient's affect area. Treatment component 300 then administers the appropriate dose to the patients affected area to destroy the abnormal cells. After treatment, the medical professional again uses diagnostic component 200 to evaluate the fluorescence of the cells in the affected area to verify that the photosensitizer has been fully used and to verify the effectiveness of the photodynamic therapy.

The patient can undergo further diagnosis and treatment with diagnostic and therapeutic device 10 until the abnormal cells in the patient's affected area are destroyed.

In an alternate aspect of the invention, FIGS. 28-35 depict photodiagnostic and photodynamic therapeutic device 1010. Device 1010 includes a diagnostic component 1200 for optical detection of lesions, a treatment component 1300 for treatment of lesions, a control component 1400 to control diagnostic component 1200 and treatment component 1300, and an adjustable support 1500 on mobile base 1600. Diagnostic component 1200 includes all the features of diagnostic component 200, e.g., as discussed above. Treatment component 1300 includes all the features of treatment component 300, e.g., as discussed above. Control component 1400 includes all the features of control component 400, e.g., as discussed above.

Adjustable support 1500 allows for positioning of diagnostic component 1200 or treatment component 1300 to allow for accurate positioning of light to the cervical area during diagnosis or treatment. Support 1500 includes a coupling 1510 to attach to diagnostic component 1200 or treatment component 1300. Support 1500 includes adjustment locks 1520*a* and 1542*a* and telescopic member 1542 to regulate the height and position of coupling 1510 for positioning of diagnostic component 1200 or treatment component 1300. Support 1500 also includes flexible rod 1530 for fine adjustments to the positioning of diagnostic component 1200 or treatment component 1300. In one aspect of the invention, support 1500 allows for a variable height ranging from approximately 80 cm to approximately 140 cm. Support 1500 also includes cable supports 1502*a* and 1502*h* to retain a power cord for photo diagnostic and photodynamic therapeutic device 1010. Support 1500 also includes control component supports 1504*a* and 1504*b* to retain control component 1400 on support 1500. Support 1500 is attached to mobile base 1600. Mobile base 1600 includes wheels 1602 and feet 1620. Mobile base 1600 allows photo diagnostic and photodynamic therapeutic device 1010 to be easily maneuvered into place for use.

Control component 1400 includes control component shell 1450, power outlet 1402, and master on-off switch 1404. Control component 1400 includes cable support 1418. Control component 1400 also includes interlock 1422 to prevent unauthorized access to control component 1400. Control component 1400 provides power to diagnostic component 1200 and/or treatment component 1300 through power cords 1252 and 1306, respectively. Control component 1400 includes two way connector 1460*a* to connect to power cord 1306. Control component 1400 also includes four way connector 1460*b* to connect to power cord 1252. Control component 1400 further includes treatment component support 1430 and/or diagnostic component support 1420 which retain the respective components when not in use. Control component 1400 also includes control panel 1408 which includes the same features as control panel 408 discussed above. For example, control panel 1408 includes display screen 1410 and operation buttons 1412, 1414, 1416*a*, and 1416*b*. Control panel 1408 controls the operation of diagnostic component 1200 and/or treatment component 1300. Control panel 1408 allows the medical professional to select for use of either diagnostic component 1200 or treatment component 1300

Treatment component 1300 utilizes high intensity LEDs to treat a patient's affected area. Treatment component 1300 includes light component 1304 and guiding sleeve 370. In this aspect of the invention, guiding sleeve 370 is positioned approximately 90 degrees relative to light component 1304. In alternate aspects of the invention, guiding sleeve 370 can be positioned at a number of different angles relative to light component 1304. For example, guiding sleeve 370 can be positioned from approximately 0 degrees to approximately 140 degrees relative to light component 1304. When treatment component 1300 is not in use, guiding sleeve 370 can be removed and replaced with end cap 1352. End cap 1352 can be attached to light component shell 1350 and can cover the light emitting end of light component 1304. In one aspect of the invention, end cap 1352 contains interior threads for a threaded engagement to shell 1350. In an alternate aspect of the invention, end cap 1352 can also be attached to shell 1350 by an interference engagement or other suitable attachment.

High-intensity LEDs 1322 are located on core metal plate 1320 near the bottom portion of light component 1304. Core metal plate 1320 allows for the high-intensity LEDs 1322 to be distributed circularly in light component 1304 and to have an emission of a specified wavelength or range of wavelengths corresponding to the absorption spectrum of one or more photosensitizers in a range of approximately 400 nm to approximately 820 nm, similar to high-intensity LEDs 322, discussed above. In an alternate aspect of the invention, core metal plate 1320 can contain multiple LEDs that emit light at different wavelengths. In this aspect, the medical professional can select the appropriate wavelength for a particular photosensitizer by selectively activating the appropriate LEDs.

In addition, treatment component 1300 can generate a continuous variation of light intensities, similar to treatment component 300, ranging from approximately 0 mW/cm$^2$ to approximately 250 mW/cm$^2$, based on the operating range of high-intensity LEDs 1322. In an alternate aspect of the invention, treatment component 1300 can generate a continuous variation of light intensities ranging from approximately 40 mW/cm$^2$ to approximately 120 mW/cm$^2$.

Protective screen 1330 is positioned adjacent to high-intensity LEDs 1322 to protect the LEDs 1322 from dust and dirt and other contaminates. High-intensity LEDs 1322 generate a large amount of heat. Therefore, light component 1304 includes heat sink 1336 positioned adjacent to core metal plate 1320. Heat sink 1336 is designed to increase the surface area in contact with the air surrounding LEDs 1322, thus cooling the system. In one aspect of the invention, heat sink 1336 is made of metal, e.g. aluminum, or other material suitable for the transfer of thermal energy. Heat sink 1336 can also provide electrical contact between power chord 1306 and core metal plate 1320. Heat sink ring 1334 is provided and can attach heat sink 1336 to shell 1350. Insulator ring 1326 is provided between heat sink 1336 and heat sink ring 1334.

Heat sink 1336 abuts core metal plate 1320 in order to dissipate the heat generated by high-intensity LEDs 1322. Ring 1334 fastens and holds heat sink 1336 to shell 1350. Power is supplied to light component 1304 through power cord 1306.

When in use, end cap 1352 is removed and guiding sleeve 370 is attached to light component 1304 at guiding sleeve nozzle 1310. As discussed above, guiding sleeve 370 is composed of light guide 380, protective sleeve 378, and light protector 372 and directs the light from high-intensity LEDs 1322 to the patient's affected area.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way. The breadth and scope of the present invention should not be limited by any of the described exemplary embodiments, but should be defined only in accordance with the following claims and their equivalents.

EXAMPLES

The following Examples are provided to illustrate, not to limit, aspects of the present invention.

Example 1

A Photosensitizer Compound and Carrier

The photosensitizer can be mixed into a cream for application to a patient's affected area. The cream can contain MAL (methyl aminolevulinic acid) 20% (w/w) homogenized in with POLAWAX 19.5%; CETIOL V (decyl oleate) 4%; NIPASOL (propyl paraben) 0.2%; dimethyl sulfoxide (DMSO) 5%; NIPAGIN (sodium methyl paraben) 0.15%; propylene glycol 5%; ethylenediamine tetraacetic acid (EDTA) 0.15%; butylated hydroxytoluene (BHT) 0.05%; GERMAL (imidazolinol urea) 0.2% and deionized water, enough to homogenize the constituents.

To prepare the cream, the oil phase containing POLAWAX, CETIOL V and NIPASOL and the aqueous phase containing NIPAGIN, propylene glycol, EDTA, BHT, and GERMAL are weighed and heated to approximately 65 to approximately 70 degrees centigrade. Next, the aqueous phase is poured into the oily phase with constant stirring while also incorporating the DMSO. Next the mixture is shaken to form the cream. The MAL (20 g) is mixed with 80 g of the cream.

In this mixture, POLAWAX is an emulsifying wax; DMSO is an organic compound that assists MAL penetration into the tissue; NIPASOL (propyl paraben), NIPAGIN (sodium methyl paraben), and GERMAL (imidazolinol urea) are antifungal and antimicrobial agents; propylene glycol and decyl oleate are emollient agents; EDTA is an iron chelating agent; and BHT is an antioxidant compound.

Example 2

FIGO Cervical Cancer Staging

The diagnostic and therapeutic device 10 can treat cervical dysplasia (cervical intraepithelial neoplasia (CIN); precancerous changes of the cervix, including HPV lesions), stage I cervical cancer including stages IA (IA1, and IA2), as defined by the International Federation of Gynecology and Obstetrics (FIGO). According to FIGO staging, in stage I cervical cancer, the cancer has grown into (invaded) the cervix, but it is not growing outside the uterus. The cancer has not spread to nearby lymph nodes (N0) or distant sites (M0). In stage IA, there is a very small amount of cancer, and it can be seen only under a microscope. In stage IA1, the cancer is less than 3 mm deep and less than 7 mm wide. In stage IA2, the cancer is between 3 mm and 5 mm deep and less than 7 mm wide.

Example 3

Diagnosis and Detection

Diagnostic component 200 allows a medical professional to noninvasively detect existing differences between healthy tissue and abnormal tissue. Diagnostic component 200 can detect autofluorescence of the abnormal tissue, fluorescence of the abnormal tissue after the photosensitizer is applied, or fluorescence of the abnormal tissue after treatment with treatment component 300. An example of tissue autofluorescence of Grade II cervical dysplasia as detected by diagnostic component 200 is provided in FIG. 13. An example of tissue fluorescence of Grade I cervical dysplasia after use of a photosensitizer as detected by diagnostic component 200 is provided in FIG. 14. An example of tissue fluorescence of Grade I cervical dysplasia after treatment with treatment component 300 as detected by diagnostic component 200 is provided in FIG. 15.

Example 4

Treatment

Figure 14:
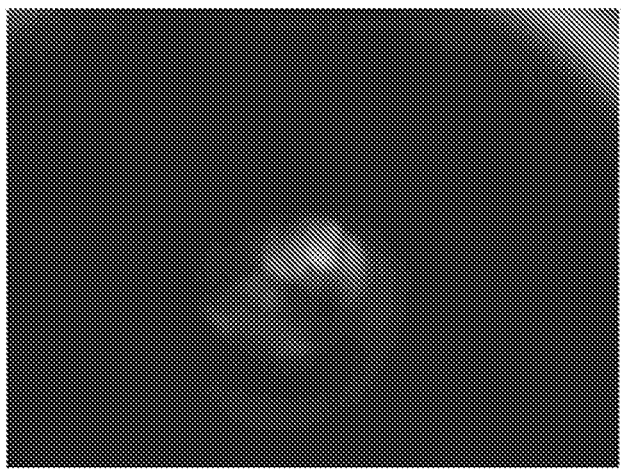
FIG. 14 is an image representing tissue fluorescence as shown by a photodynamic treatment component of the photodiagnostic and photodynamic therapeutic device, in accordance with an exemplary aspect of the invention.
Figure 15:
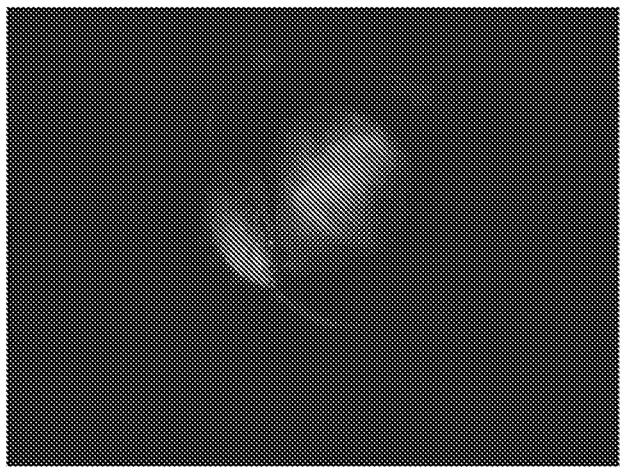
FIG. 15 is an image representing tissue fluorescence as shown by a photodynamic treatment component of the photodiagnostic and photodynamic therapeutic device, in accordance with an exemplary aspect of the invention.

To date, twenty-three patients have been diagnosed with and successfully treated for cervical precancer (cervical intraepithelial carcinoma) using a device that includes the diagnostic component and the treatment component. FIG. 15 ("Fluorescence after treatment") shows successful treatment. FIG. 14 shows an area of fluorescence in the upper portion that is no longer visible after treatment in FIG. 15. On the basis of this data, the device will soon enter clinical trials.

A recent finding demonstrates that "a discrete population of squamocolumnar junction cells is implicated in the pathogenesis of cervical cancer." See Herfs et al., "A discrete population of squamocolumnar junction cells implicated in the pathogenesis of cervical cancer," *PNAS* 109: 10516-10521 (2012). This finding shows that these squamocolumnar junction cells are found on the ectoendocervical junction and may be a source for cervical cancer. Such a finding explains the effectiveness of treatment using the present invention because the photodiagnostic and photodynamic therapeutic device disclosed herein detects and treats these pre-cancerous cells on the ectoendocervical junction. The photosensitizer penetrates the junction and the treatment component destroys the abnormal cells in that area (junction).

Each cited patent and publication is incorporated herein by reference in its entirety for all purposes.

What is claimed is:
1. A system, comprising:
    a photodiagnostic component, including a laser light source, at least one lens, and at least one light filter, wherein the photodiagnostic component is adapted to generate and direct a first wavelength of light toward cervical tissue and to separate a spectral region of light from a fluorescence of light reflected by the cervical tissue;
    a photodynamic treatment component, including a second light source comprising a plurality of light emitting diodes (LEDs), each LED configured to emit light at a different wavelength within a range of approximately 400 nm to approximately 820 nm, and a light guide, wherein the photodynamic treatment component is adapted to generate light at a second wavelength and to direct the second wavelength of light onto the cervical tissue; and
    a control component attached to the photodiagnostic component and the photodynamic treatment component providing power to the photodiagnostic component and the photodynamic treatment component and controlling activation of the laser light source and the second light source.
2. The system of claim 1, wherein the photodiagnostic component comprises:
    an element in thermal contact with the laser light source configured to regulate the temperature of the laser light source; and
    an optic having a light pathway;
    wherein the at least one light filter includes a first light filter disposed along the light pathway to direct the light from the lens to an end of the light pathway toward the cervical tissue, and a second light filter disposed along the light pathway adapted to separate the spectral region of light from the fluorescence of light reflected by the cervical tissue.
3. The system of claim 2, wherein the second light filter is a high pass filter.
4. The system of claim 1, wherein the photodiagnostic component is hand held.

5. The system of claim 1, wherein the at least one lens includes a first lens and a second lens adapted to emit a light beam approximately 20 mm in diameter.

6. The system of claim 1, wherein each of the photodiagnostic component and the photodynamic treatment component is hand held.

7. The system of claim 1, wherein the at least one light filter is a high pass filter, and wherein the plurality of LEDs of the second light source are distributed in a circular configuration.

8. The system of claim 1, wherein the laser light source generates a light beam approximately 20 mm in diameter.

9. The system of claim 1, wherein the second light source generates a light beam approximately 20 mm in diameter, and wherein the second light source is configured to generate visible light.

10. The system of claim 1, wherein the light guide is adapted for vaginal insertion.

11. A photodynamic treatment device, comprising:
a light component including a light source and an element in thermal contact with the light source configured to regulate the temperature of the light source;
a light guide configured to be selectively detached and re-attached to the light component by inserting a proximal end of the light guide into a distal end portion of the light component, the light guide being adapted for vaginal insertion and to direct light generated by the light source to cervical tissue; and
a light protector attached to a distal end of the light guide adapted to surround the cervical tissue.

12. The photodynamic treatment device of claim 11, wherein the device produces an illumination area of approximately 20 mm in diameter.

13. The photodynamic treatment device of claim 11, further comprising:
a protective sleeve surrounding the light guide, the protective sleeve adapted for vaginal insertion; and
a ring provided between the light guide and the protective sleeve, adapted to center the protective sleeve on the light guide and to provide a biological barrier between the cervical tissue and the light source.

14. A method for treating cervical tissue, the method comprising;
selecting an appropriate dose of light energy of a photodynamic treatment device, the device comprising:
a light component including a light source and an element in thermal contact with the light source configured to regulate the temperature of the light source;
a rigid light guide attached to the light component, wherein the rigid light guide is configured to be selectively detached and re-attached to the light component by inserting a proximal end of the light guide into a distal end portion of the light component; and
a light protector attached to a distal end of the light guide;
inserting the light guide into a vagina such that the light protector surrounds a portion of cervical tissue, wherein the cervical tissue has a photosensitizer compound disposed thereon;
generating a light emission with the light source; and
directing the light emission through the light guide to the cervical tissue for a selected period of time to deliver the selected dose of light energy to the cervical tissue.

15. The method of claim 14, wherein an area illuminated by the light emission is approximately 20 mm in diameter.

16. A method of diagnosing and treating abnormal cervical tissue, comprising:
analyzing cervical tissue by generating a laser light emission, directing the laser light emission toward the cervical tissue, passing light received from the cervical tissue through a light filter to separate fluorescence of the cervical tissue, and viewing the fluorescence of the cervical tissue to detect the presence of abnormal cervical tissue; and
treating the abnormal cervical tissue having a photosensitizer compound disposed thereon by generating a second light emission and directing the second light emission toward the cervical tissue through a rigid guiding sleeve to deliver a selected dose of light energy to destroy the abnormal cervical tissue, wherein a distal end of the guiding sleeve is coupled to a light protector adapted to contact the cervical tissue.

17. The method of claim 16, further comprising:
after treating the abnormal cervical tissue, analyzing the cervical tissue by generating a second laser light emission, directing the second laser light emission toward the cervical tissue, passing the second laser light emission through the light filter, and viewing the fluorescence of the cervical tissue to detect the presence or absence of abnormal cervical tissue.

18. A method of treating cervical tissue, comprising:
analyzing the cervical tissue with a hand-held photodiagnostic device coupled to a control component, the photodiagnostic device comprising a laser light source, a collimating lens, a first light filter, a second light filter, a circuit board, and a viewing window, wherein analyzing the cervical tissue comprises:
generating light from the laser light source, wherein the circuit board communicates with the control component to control an intensity of the light and a wavelength of the light;
directing the light through the collimating lens;
directing light from the collimating lens through the first filter towards the cervical tissue;
separating a spectral region of light received from the cervical tissue; and
viewing fluorescence from the cervical tissue through the viewing window; and
treating the cervical tissue with a hand-held photodynamic treatment device coupled to the control component, the photodynamic treatment device comprising a light component, a light guide removably attached to the light component and adapted for vaginal insertion, and a light protector attached to the distal end of the light guide, wherein treating the cervical tissue comprises:
selecting an appropriate dose of light energy of the photodynamic treatment device via the control component;
generating light from a plurality of light emitting diodes (LEDs) of the light component; and
directing the light from the plurality of LEDs through the light guide to the cervical tissue for a selected period of time to deliver the selected dose of energy;
wherein the control component includes a manual operating mode and a protocol operating mode for selectively controlling an intensity of light emitted by the photodynamic treatment device.

19. The method of claim 18, wherein analyzing the cervical tissue further comprises identifying an area of abnormal cervical tissue based on the fluorescence of the cervical tissue, and applying a photosensitizer compound to the area.

20. The method of claim 18, wherein selecting the appropriate dose of light energy of the photodynamic treatment device comprises selecting a treatment protocol via a user interface of the control component, the treatment protocol controlling the intensity of light emitted by the photodynamic treatment device for a predetermined amount of time.

* * * * *